United States Patent
Aractingi et al.

(10) Patent No.: US 11,406,686 B2
(45) Date of Patent: Aug. 9, 2022

(54) METHODS FOR THE TREATMENT OF TISSUE LESIONS WITH CCR2 AGONISTS

(71) Applicants: INSERM (INSTITUT NATIONAL DE LA SANTE ET DE LA RECHERCHE MEDICALE), Paris (FR); SORBONNE UNIVERSITE, Paris (FR); UNIVERSITE PARIS DESCARTES, Paris (FR); ASSISTANCE PUBLIQUE-HOPITAUX DE PARIS (APHP), Paris (FR)

(72) Inventors: Selim Aractingi, Paris (FR); Mathieu Catela, Paris (FR); Dany Nassar, Paris (FR); Zhe Wang, Paris (FR)

(73) Assignees: INSERM (Institut National de la Santé et de la Recherche Médicale), Paris (FR); Sorbonne Université, Paris (FR); Université Paris Descartes, Paris (FR); Assistance Publique-Hôpitaux de Paris (APHP), Paris (FR)

( * ) Notice: Subject to any disclaimer, the term of this patent is extended or adjusted under 35 U.S.C. 154(b) by 795 days.

(21) Appl. No.: 16/098,689

(22) PCT Filed: May 2, 2017

(86) PCT No.: PCT/EP2017/060351
§ 371 (c)(1),
(2) Date: Nov. 2, 2018

(87) PCT Pub. No.: WO2017/191100
PCT Pub. Date: Nov. 9, 2017

(65) Prior Publication Data
US 2021/0268068 A1    Sep. 2, 2021

(30) Foreign Application Priority Data
May 3, 2016  (EP) .................................... 16305512

(51) Int. Cl.
| | | |
|---|---|---|
| *A61K 38/19* | (2006.01) | |
| *A61P 19/02* | (2006.01) | |
| *A61P 17/02* | (2006.01) | |
| *A61K 45/06* | (2006.01) | |
| *C07K 16/28* | (2006.01) | |
| *C12N 15/115* | (2010.01) | |
| *G01N 33/50* | (2006.01) | |
| *A61K 47/68* | (2017.01) | |
| *A61K 39/395* | (2006.01) | |
| *C07K 14/52* | (2006.01) | |
| *A61K 39/00* | (2006.01) | |

(52) U.S. Cl.
CPC ........ *A61K 38/195* (2013.01); *A61K 39/3955* (2013.01); *A61K 45/06* (2013.01); *A61K 47/68* (2017.08); *A61P 17/02* (2018.01); *C07K 16/2866* (2013.01); *C12N 15/115* (2013.01); *G01N 33/502* (2013.01); *A61K 2039/505* (2013.01); *C07K 14/523* (2013.01); *C07K 2317/21* (2013.01); *C07K 2317/24* (2013.01); *C07K 2317/75* (2013.01); *C12N 2310/16* (2013.01)

(58) Field of Classification Search
CPC ...... C07K 14/523; A61K 38/195; A61P 17/02
See application file for complete search history.

(56) References Cited

U.S. PATENT DOCUMENTS

2013/0323245 A1* 12/2013 Lillard, Jr. ........... C07K 14/521
424/134.1

FOREIGN PATENT DOCUMENTS

WO    WO-2015138288 A1 *  9/2015   ............. A61K 45/06

OTHER PUBLICATIONS

Wood et al (2014. PLos One. 9(3): e91574; pp. 1-8 as printed).*
Jeffcoate et al, 2003. The Lancet. 361(9368): 1545-1551.*
Tokuriki et al, 2009, Current Opinion in Structural Biology. 19: 596-604.*
Bhattacharya et al, 2017. Plos One. 12(3): e0171355, pp. 1-22 as printed.*
Castela et al (2017, Nature Communications. 8:15463).*
Hoh Brina L et al: "Monocyte chemotactic protein-1 promotes inflammatory vascular repair of murine carotid aneurysms via a macrophage inflammatory protein-1[alpha] and macrophage inflammatory protein-2-dependent pathway", Ciruclation, Lippincot Williams and Wilkins, Baltimore, US, vol. 124, No. 20, pp. 2243-2252, Nov. 1, 2011.

(Continued)

*Primary Examiner* — Zachary C Howard
(74) *Attorney, Agent, or Firm* — WCF IP

(57) ABSTRACT

The present invention relates to methods and pharmaceutical compositions for the treatment of tissue lesions. The inventors showed that CCR2 is expressed on FMCs, especially on a subpopulation of progenitor cells, that they call "fetal myeloid progenitor cells" (FMPCs), and mediates the recruitment of these cells to maternal wound tissue. Moreover, the inventors reported that recruited FMCs/FMPCs improve maternal skin wound healing by organizing blood vessel endothelium and secreting pro-angiogenesis peptides, particularly chemokine CXCL1, to enhance angiogenesis in wound. In particular, the present invention relates to CCR2 agonists for use in the treatment of tissue lesions in a subject in need thereof.

Figure 1A:
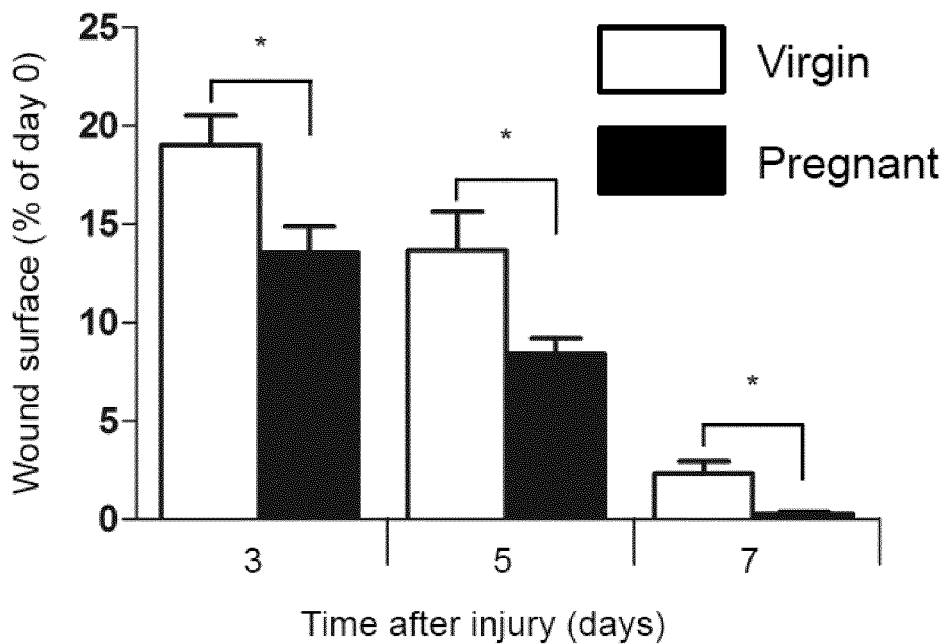

11 Claims, 28 Drawing Sheets
Specification includes a Sequence Listing.

(56) References Cited

OTHER PUBLICATIONS

Weber Kim S C et al: "Expression of CCR2 by endothelial cells: Implications for MCP-1 mediated wound injury repair and in vivo inflammatory activation of endothelium", Aeteriosclerosis, Thrombosis, and Vacular Biology, Lippincott Willams & Wilkins, US, vol. 19, No. 9, pp. 2085-2093, Sep. 1, 1999.
Quentin E H Low et al: "Wound healing in MIP-1alpha(−/−) and MCP-1(−/−) mice", American Journal of Pathology, vol. 159, No. 2, pp. 457-463, Aug. 1, 2001.
Geoffrey C. Gurtner et al: "Wound repair and regeneration", Nature, vol. 453, No. 7193, pp. 341-321, May 15, 2008.

* cited by examiner

METHODS FOR THE TREATMENT OF TISSUE LESIONS WITH CCR2 AGONISTS

FIELD OF THE INVENTION

The present invention relates to methods and pharmaceutical compositions for the treatment of tissue lesions.

BACKGROUND OF THE INVENTION

Tissue lesions are a major concern since it may target a wide diversity of affected tissues, lesion anatomies and etiologies. Despite existing treatments, there remains a need for improved therapies and more creative approaches for treating tissue lesions.

In particular, wound healing is a process involved in many conditions, such as traumas or diseases, including vascular disorders, diabetes, steroid treatments induced changes and genetic abnormalities such as sickle-cell anaemia for example. Wound healing is an intricate and interactive biological process that includes three phases which overlap in time: inflammation, proliferation and tissue remodeling (Gurtner G C, Werner S, Barrandon Y, and Longaker M T. Wound repair and regeneration. Nature. 2008; 453 (7193): 314-21). The well-coordinated interplay between tissue structures, mass number of residential cells (keratinocytes, fibroblasts and endothelial cells) and infiltrating immunocytes (neutrophils, macrophages and lymphocytes) are essential for the healing process (Singer A J, and Clark R A. Cutaneous wound healing. N Engl J Med. 1999; 341 (10): 738-46). Fetal microchimeric cells (FMCs) have been reported to participate in maternal wound healing when adult mothers have been pregnant (Nassar D, Droitcourt C, Mathieu-d'Argent E, Kim M J, Khosrotehrani K, and Aractingi S. Fetal progenitor cells naturally transferred through pregnancy participate in inflammation and angiogenesis during wound healing. FASEB J. 2012; 26(1):149-57) (Seppanen E, Roy E, Ellis R, Bou-Gharios G, Fisk N M, and Khosrotehrani K. Distant mesenchymal progenitors contribute to skin wound healing and produce collagen: evidence from a murine fetal microchimerism model. PLoS One. 2013; 8 (5):e62662).

Indeed, FMCs, enter maternal circulation during all pregnancies in humans and rodents, and persist in maternal marrow for the remainder of the lifespan after delivery (O'Donoghue K, Chan J, de la Fuente J, Kennea N, Sandison A, Anderson J R, Roberts I A, and Fisk N M. Microchimerism in female bone marrow and bone decades after fetal mesenchymal stem-cell trafficking in pregnancy. Lancet. 2004; 364 (9429):179-82). These cells have been reported to include a heterogeneous population of progenitor cells namely lymphoid, hematopoietic and mesenchymal progenitors: these may differentiate in various maternal tissues in cardiomyocytes, neurons, hepatocytes, fibroblasts, endothelial cells, leukocytes, thyroid, cervix and gut epithelial cells etc. These cells are able to seed in variable proportion different maternal organs (Fujiki Y, Johnson K L, Peter I, Tighiouart H, and Bianchi D W. Fetal cells in the pregnant mouse are diverse and express a variety of progenitor and differentiated cell markers. Biol Reprod. 2009; 81 (1):26-32). Indeed, fetal cells are discovered in high frequency in injured tissues (Khosrotehrani K, Johnson K L, Cha D H, Salomon R N, and Bianchi D W. Transfer of fetal cells with multilineage potential to maternal tissue. JAMA. 2004; 292 (1):75-80). FMCs have therefore been identified in acute and chronic wounds, inflamed skin, tumors such as melanoma and carcinoma, participating in blood vessel endothelium in maternal affected tissues. These data indicate the transfer of fetal endothelial progenitor cells during pregnancy and their involvement in later maternal neovascularization and wound healing process.

Chemokines are small signal proteins secreted by cells, which can direct chemotaxis movement for nearby responsive cells and play a crucial role for tissue homeostasis. CCL2, also named monocyte chemotactic protein 1 (MCP-1) is a member of CC chemokine family, secreted by monocytes and macrophages, exerts its potent chemotaxis ability for monocytes, T lymphocytes, macrophages, natural killer (NK) cells and endothelial cells. The major receptor for CCL2 is CCR2 and it is highly expressed on the surface of various cells, including monocytes, macrophages, endothelial cells. CCL2 attracts target cells through binding strongly to CCR2 on their surface and mediates chemotactic function (Boring L, Gosling J, Chensue S W, Kunkel S L, Farese R V, Jr., Broxmeyer H E, and Charo I F. Impaired monocyte migration and reduced type 1 (Th1) cytokine responses in C-C chemokine receptor 2 knockout mice. J Clin Invest. 1997; 100(10):2552-61).

Because of the presence of their receptors on various immunocytes and residential cells, chemokines play crucial roles in all three phases of wound healing: not only to direct the recruitment of leukocytes during early inflammatory phase but also to contribute to angiogenesis, re-epithelialization and tissue remodeling during the later steps (Gillitzer R, and Goebeler M. Chemokines in cutaneous wound healing. J Leukoc Biol. 2001; 69(4):513-21). CCL2 participates to wound healing process, especially during the early stage (Engelhardt E, Toksoy A, Goebeler M, Debus S, Brocker E B, and Gillitzer R. Chemokines IL-8, GROalpha, MCP-1, IP-10, and Mig are sequentially and differentially expressed during phase-specific infiltration of leukocyte subsets in human wound healing. Am J Pathol. 1998; 153(6):1849-60). Overexpression of CCL2 has been reported in human burn wound (Gibran N S, Ferguson M, Heimbach D M, and Isik F F. Monocyte chemoattractant protein-1 mRNA expression in the human burn wound. J Surg Res. 1997; 70(1):1-6). Deficiency of CCL2, together with other chemokines, resulted in impaired recruitment of myeloid cells and skin healing (Lin Q, Fang D, Fang J, Ren X, Yang X, Wen F, and Su S B. Impaired wound healing with defective expression of chemokines and recruitment of myeloid cells in TLR3-deficient mice. J Immunol. 2011; 186(6):3710-7), while in the same way full CCL2 deficiency causes delayed myocardial infarcts healing (Dewald O, Zymek P, Winkelmann K, Koerting A, Ren G, Abou-Khamis T, Michael L H, Rollins B J, Entman M L, and Frangogiannis N G. CCL2/Monocyte Chemoattractant Protein-1 regulates inflammatory responses critical to healing myocardial infarcts. Circ Res. 2005; 96(8):881-9). These data indicate that the presence of CCL2 is mandatory for normal healing. However, injection of CCL2 at various doses in normal recipients do not modify wound healing (Di Pietro, 2001). In contrast, CCL2 administration improves wound healing when there is a defect in CCL2 secretion such as in diabetic wound (Wood S, Jayaraman V, Huelsmann E J, Bonish B, Burgad D, Sivaramakrishnan G, Qin S, DiPietro L A, Zloza A, Zhang C, et al. Pro-inflammatory chemokine CCL2 (MCP-1) promotes healing in diabetic wounds by restoring the macrophage response. PLoS One. 2014; 9(3):e91574). CCR2, the CCL2 receptor, mediates monocytes, macrophages Ly6C+ and hematopoietic progenitor cells migrating from bone marrow to blood and then to injured or inflammed tissues. Therefore, the CCL2/CCR2 pathway mediates recruitment of immunocytes and marrow cells that have well been established.

SUMMARY OF THE INVENTION

The present invention relates to methods and pharmaceutical compositions for the treatment of tissue lesions. In particular, the invention is defined by the claims.

DETAILED DESCRIPTION OF THE INVENTION

Here, the inventors report that CCL2 is expressed mainly by leukocytes during early stages of skin wound healing. They show that CCR2 is expressed on FMCs, especially on a subpopulation of progenitor cells, that they call "fetal myeloid progenitor cells" (FMPCs), and mediates the recruitment of these cells to maternal wound tissue. Moreover, the inventors report that recruited FMCs/FMPCs improve maternal skin wound healing by organizing blood vessel endothelium and secreting pro-angiogenesis peptides, particularly chemokine CXCL1, to enhance angiogenesis in wound. Their findings suggest the pivotal role of CCL2/CCR2 signaling in recruitment of FMCs/FMPCs and their participant in maternal tissue repair.

A first aspect of the present invention relates to a method of treating a tissue lesion in a subject in need thereof comprising administering the subject with a therapeutically effective amount of a CCR2 agonist.

As used herein, the term "subject" denotes a female mammal, such as a rodent, a feline, a canine, and a primate who is pregnant or who has been pregnant at least one time. Thus, it is understood that the subject according to the present invention is not a male. Preferably the subject according to the invention is a woman. Preferably, the subject according to the present invention is a woman who is pregnant or who has been pregnant at least one time. In the context of the present invention, a "subject in need thereof" denotes a subject, preferably a woman suffering from any tissue lesion.

As used herein, the term "CCR2" for "chemokine (C-C motif) receptor 2" has its general meaning in the art and refers to a chemokine receptor. CCR2 is a member of G-protein coupled receptors superfamily and binds to the CCL2, CCL7, CCL8, CCL12, CCL13 and CCL16 chemokines. CCR2 transduces a signal by increasing intracellular calcium ion levels.

Chemokines receptor CCR2, through either of any isoform A (SEQ ID N:1), or isoform B (SEQ ID N:2):

```
SEQ ID NO: 1 (isoform A):
         10          20          30          40
MLSTSRSRFI  RNTNESGEEV  TTFFDYDYGA  PCHKFDVKQI 50          60          70          80
GAQLLPPLYS  LVFIFGFVGN  MLVVLILINC  KKLKCLTDIY 90         100         110         120
LLNLAISDLL  FLITLPLWAH  SAANEWVFGN  AMCKLFTGLY 130         140         150         160
HIGYFGGIFF  IILLTIDRYL  AIVHAVFALK  ARTVTFGVVT 170         180         190         200
SVITWLVAVF  ASVPGIIFTK  CQKEDSVYVC  GPYFPRGWNN 210         220         230         240
FHTIMRNILG  LVLPLLIMVI  CYSGILKTLL  RCRNEKKRHR 250         260         270         280
AVRVIFTIMI  VYFLFWTPYN  IVILLNTFQE  FFGLSNCEST
```

```
-continued
        290         300         310         320
SQLDQATQVT  ETLGMTHCCI  NPIIYAFVGE  KFRSLFHIAL 330         340         350         360
GCRIAPLQKP  VCGGPGVRPG  KNVKVTTQGL  LDGRGKGKSI

370
GRAPEASLQD  KEGA

SEQ ID NO: 2 (isoform B):
         10          20          30          40
MLSTSRSRFI  RNTNESGEEV  TTFFDYDYGA  PCHKFDVKQI 50          60          70          80
GAQLLPPLYS  LVFIFGFVGN  MLVVLILINC  KKLKCLTDIY 90         100         110         120
LLNLAISDLL  FLITIPLWAH  SAANEWVFGN  AMCKLFTGLY 130         140         150         160
HIGYFGGIFF  IILLTIDRYL  AIVHAVFALK  ARTVTFGVVT 170         180         190         200
SVITWLVAVF  ASVPGIIFTK  CQKEDSVYVC  GPYFPRGWNN 210         220         230         240
FHTIMRNILG  LVLPLLIMVI  CYSGILKTLL  RCRNEKKRHR 250         260         270         280
AVRVIFTIMI  VYFLFWTPYN  IVILLNTFQE  FFGLSNCEST 290         300         310         320
SQLDQATQVT  ETLGMTHCCI  NPIIYAFVGE  KFRRYLSVFF 330         340         350         360
RKHITKRFCK  QCPVFYRETV  DGVTSTNTPS  TGEQEVSAGL
```

As used herein, the term "CCR2 agonist" refers to any compound, natural or not, that is able to bind to CCR2 and promotes CCR2 activity.

As used herein, the term "tissue lesion" relates to abnormal biological tissue change or damage in the tissue of an organism, usually caused by disease or trauma. It may be a cut, a burn, a wound, or also resulting from the action of a pathogen such as parasite or infection as well as metabolic, physiological, vascular, genetic or immune disorder.

In some embodiment, the tissue lesion is selected from the group consisting of skin lesion, hepatic lesion, cardiac lesion, lung lesion, neurologic lesion, ocular lesion, stomach lesion, pancreas lesion, spleen lesion, bowel lesion, thyroid lesion, thymus lesion, kidney lesion, artery lesion, vein lesion, bone lesion, bone marrow lesion, muscle lesion, tendon lesion, ligament lesion, reproductive organs lesion or endocrine glands lesion.

In some embodiment, the tissue lesion is selected from the group consisting of skin lesion, hepatic lesion, cardiac lesion, lung lesion, neurologic lesion, ocular lesion, stomach lesion, pancreas lesion, spleen lesion, bowel lesion, thyroid lesion, thymus lesion, kidney lesion, artery lesion except carotid aneurysm, vein lesion, bone lesion, bone marrow lesion, muscle lesion, tendon lesion, ligament lesion, reproductive organs lesion or endocrine glands lesion.

In some embodiments, the tissue lesion is a diabetic foot ulcer resulting from diabetes.

In some embodiment, the tissue lesion is leg ulcer resulting from sickle-cell anemia.

In some embodiment, the tissue lesion is leg ulcer resulting from micro or macro vascular disease.

In some embodiments, the tissue lesion results from sickle-cell disease.

It is to be understood that the term "wound" as used herein includes surgical incisions as well as wounds caused by accidental trauma or pathologies.

The term also includes venous stasis ulcer, burns, delayed wound healing observed during corticoid treatments, delayed wound healing observed in elderly (aging defect), stress, delayed wound healing observed in diabetic patients, epithelialization defects of surgical scars or following skin grafts, finger cracks occurring after cold exposure, nail pathologies associated with delayed healing, foot blisters occurring during prolonged walk or run.

Corneal wounds may result from observed various diseases such as corneal ulcer, corneal erosion or trauma, keratitis and dry eye. Wound may also result from topical administration of drugs and surgery situations, such as keratoplasty and during the time-course of recovery from corneal graft.

In particular, the term "wound" as used herein refers to any wound resulting from diabetes, such as diabetic foot ulcer or to any wound resulting from sickle-cell anaemia, such as leg ulcer.

As used herein, the terms "treating" or "treatment" refer to both prophylactic or preventive treatment as well as curative or disease modifying treatment, including treatment of subject at risk of contracting the disease or suspected to have contracted the disease as well as subject who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

In some embodiments, the CCR2 agonist is a small organic molecule. The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more in particular up to 2000 Da, and most in particular up to about 1000 Da.

In some embodiments, the CCR2 agonist is a CCR2 antibody or a portion thereof. In some embodiments, the CCR2 agonist is selected from the group consisting of chimeric antibodies, humanized antibodies or full human monoclonal antibodies.

As used herein, "antibody" includes both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man.

In one embodiment of the antibodies or portions thereof described herein, the antibody is a monoclonal antibody. In one embodiment of the antibodies or portions thereof described herein, the antibody is a polyclonal antibody. In one embodiment of the antibodies or portions thereof described herein, the antibody is a humanized antibody. In one embodiment of the antibodies or portions thereof described herein, the antibody is a chimeric antibody. In one embodiment of the antibodies or portions thereof described herein, the portion of the antibody comprises a light chain of the antibody. In one embodiment of the antibodies or portions thereof described herein, the portion of the antibody comprises a heavy chain of the antibody. In one embodiment of the antibodies or portions thereof described herein, the portion of the antibody comprises a Fab portion of the antibody. In one embodiment of the antibodies or portions thereof described herein, the portion of the antibody comprises a F(ab')2 portion of the antibody. In one embodiment of the antibodies or portions thereof described herein, the portion of the antibody comprises a Fc portion of the antibody. In one embodiment of the antibodies or portions thereof described herein, the portion of the antibody comprises a Fv portion of the antibody. In one embodiment of the antibodies or portions thereof described herein, the portion of the antibody comprises a variable domain of the antibody. In one embodiment of the antibodies or portions thereof described herein, the portion of the antibody comprises one or more CDR domains of the antibody.

Antibodies are prepared according to conventional methodology. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with antigenic forms of CCR2. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes. Briefly, the recombinant CCR2 may be provided by expression with recombinant cell lines. In particular, CCR2 may be provided in the form of human cells expressing CCR2 at their surface. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDRS). The CDRs, and in particular the CDRS regions, and more particularly the heavy chain CDRS, are largely responsible for antibody specificity.

It is now well-established in the art that the non CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

This invention provides in certain embodiments compositions and methods that include humanized forms of antibodies. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585, 089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., /. Mol. Biol. 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab') 2 Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

In another embodiment, the antibody according to the invention is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®".

In some embodiments, the CCR2 agonist is a polypeptide. In a particular embodiment the polypeptide is a functional equivalent of CCL2.

As used herein, the term "CCL2" refers to the chemokine (C-C motif) ligand 2, also referred as monocyte chemotactic protein 1 (MCP1) and small inducible cytokine A2. CCL2 is a small cytokine that belongs to the CC chemokine family.

In some embodiments, the present invention provides a polypeptide which comprises consecutive amino acids having a sequence which corresponds to the sequence of at least a portion of CCL2, which portion binds to CCR2 and promotes the CCR2 activity according to the invention.

The polypeptides of the invention may be produced by any suitable means, as will be apparent to those of skill in the art. In order to produce sufficient amounts of polypeptides or functional equivalents thereof for use in accordance with the present invention, expression may conveniently be achieved by culturing under appropriate conditions recombinant host cells containing the polypeptide of the invention. In particular, the polypeptide is produced by recombinant means, by expression from an encoding nucleic acid molecule. Systems for cloning and expression of a polypeptide in a variety of different host cells are well known. When expressed in recombinant form, the polypeptide is in particular generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells. HeLa cells, baby hamster kidney cells and many others. Bacteria are also preferred hosts for the production of recombinant protein, due to the ease with which bacteria may be manipulated and grown. A common, preferred bacterial host is *E coli*.

In some embodiments, the polypeptide of the invention is an immunoadhesin.

As used herein, the term "immunoadhesin" designates antibody-like molecules which combine the binding specificity of a heterologous protein (an "adhesin" which is able to bind to CCR2) with the effector functions of immuno-

```
CCL2 (SEQ ID NO: 3):
    1 MKVSAALLCL LLIAATFIPQ GLAQPDAINA PVTCCYNFTN RKISVQRLAS

51 YRRITSSKCP KEAVIFKTIV AKEICADPKQ KWVQDSMDHL DKQTQTPKT
```

As used herein, a "functional equivalent of CCL2" is a polypeptide which is capable of binding to CCR2, thereby promoting a CCR2 activity according to the invention. The term "functional equivalent" includes fragments, mutants, and muteins of CCL2. The term "functionally equivalent" thus includes any equivalent of CCL2 obtained by altering the amino acid sequence, for example by one or more amino acid deletions, substitutions or additions such that the protein analogue retains the ability to bind to CCR2 and promote an CCR2 activity according to the invention. Amino acid substitutions may be made, for example, by point mutation of the DNA encoding the amino acid sequence.

In some embodiments, the functional equivalent of a polypeptide is at least 80% homologous to the corresponding protein.

In some embodiments, the functional equivalent of a polypeptide is at least 80%, 81%, 82%, 83%, 84%, 85%, 86%, 87%, 88%, 89%, 90%, 91%, 92%, 93%, 94%, 95%, 96%, 97%, 98% or 99% homologous to the corresponding protein.

In some embodiments, the CCR2 agonist is a polypeptide having at least 80% of identity with SEQ ID NO:3.

In a preferred embodiment, the functional equivalent of a polypeptide is at least 90% homologous as assessed by any conventional analysis algorithm such as for example, the Pileup sequence analysis software (Program Manual for the Wisconsin Package, 1996).

globulin constant domains. Structurally, the immunoadhesins comprise a fusion of an amino acid sequence with the desired binding specificity to CCR2 (i.e., is "heterologous"), and an immunoglobulin constant domain sequence. The adhesin part of an immunoadhesin molecule typically is a contiguous amino acid sequence comprising at least the binding site for CCR2. In one embodiment, the adhesin comprises the polypeptides characterized by SEQ ID NO:3. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The immunoglobulin sequence typically, but not necessarily, is an immunoglobulin constant domain (Fc region). Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use.

The polypeptides of the invention, fragments thereof and fusion proteins (e.g. immunoadhesin) according to the invention can exhibit post-translational modifications, including, but not limited to glycosylations, (e.g., N-linked or O-linked glycosylations), myristylations, palmitylations, acetylations and phosphorylations (e.g., serine/threonine or tyrosine).

In specific embodiments, it is contemplated that polypeptides used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. In example adding dipeptides can improve the penetration of a circulating agent in the eye through the blood retinal barrier by using endogenous transporters.

In one embodiment, the CCR2 agonist is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA. In this library, each member is a linear oligomer, eventually chemically modified, of a unique sequence. Peptide aptamers consists of a conformationally constrained antibody variable region displayed by a platform protein, such as *E. coli* Thioredoxin A that are selected from combinatorial libraries by two hybrid methods.

In a particular embodiment, the CCR2 agonist is CCL2.

In some embodiments, the CCR2 agonist of the invention is administered to the subject with a therapeutically effective amount.

By a "therapeutically effective amount" is meant a sufficient amount of CCR2 agonist to treat tissue lesions at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The compositions according to the invention are formulated for parenteral, transdermal, oral, rectal, subcutaneous, sublingual, intrapulmonary, topical or intranasal administration. Local administration can include simple solutions, gels, emulsions, liposomes; but also devices with patches or dressings or intra dermal or subcutaneous injections.

Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

In a particular embodiment, the pharmaceutical compositions are formulated for parenteral administration. The pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

In a particular embodiment, the pharmaceutical compositions are formulated for topical administration.

In one embodiment, the pharmaceutical compositions are formulated for being directly administrated into the lesion site.

The CCR2 agonist of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In some embodiments, the CCR2 agonist of the invention may be administered in combination with conventional treatment usually used for treating tissue lesions. For example, debridement, offloading, and infection control are conventional treatment for the treatment of ulcers in diabetes.

A further object of the invention relates to a method for screening a drug for the treatment of tissue lesions comprising the steps of i) providing a plurality of test substances ii) determining whether the test substances are CCR2 agonists and iii) positively selecting the test substances that are CCR2 agonists.

Typically, the screening method of the invention involves providing appropriate cells which express CCR2 on their surface. Such cells include cells from mammals, yeast, *Drosophila* or *E. coli*. In particular, a polynucleotide encoding CCR2 is used to transfect cells to express the receptor. The expressed receptor is then contacted with a test substance and a CCR2 ligand (e.g. CCL2), as appropriate, to observe activation of a functional response. In particular comparison steps may involve to compare the activity induced by the test substance and the activity induce by a well known CCR2 agonist such as CCL2. In particular substances capable of having an activity similar or even better than a well known CCR2 agonist are positively selected.

Typically, the screening method of the invention may also involve screening for test substances capable of binding to CCR2 present at cell surface. Typically the test substance is labelled (e.g. with a radioactive label) and the binding is compared to a well known CCR2 agonist such as CCL2.

Typically, the candidate compound is selected from the group consisting of small organic molecules, peptides, polypeptides or oligonucleotides.

The test substances that have been positively selected may be subjected to further selection steps in view of further assaying its properties for the treatment of tissue lesions. For example, the candidate compounds that have been positively selected may be subjected to further selection steps in view of further assaying its properties on animal models for tissue lesions.

The above assays may be performed using high throughput screening techniques for identifying test substances for developing drugs that may be useful to the treatment of tissue lesions. High throughput screening techniques may be carried out using multi-well plates (e.g., 96-, 389-, or 1536-well plates), in order to carry out multiple assays using an automated robotic system. Thus, large libraries of test substances may be assayed in a highly efficient manner. More particularly, stably-transfected cells growing in wells of micro-titer plates (96 well or 384 well) can be adapted to high through-put screening of libraries of compounds. Compounds in the library will be applied one at a time in an automated fashion to the wells of the microtitre dishes containing the transgenic cells described above. Once the test substances which induce the activity of CCR2 are identified, they can be positively selected for further characterization. These assays offer several advantages. The exposure of the test substance to a whole cell allows for the evaluation of its activity in the natural context in which the test substance may act. Because this assay can readily be performed in a microtitre plate format, the assays described can be performed by an automated robotic system, allowing for testing of large numbers of test samples within a reasonably short time frame. The assays of the invention can be used as a screen to assess the activity of a previously untested compound or extract, in which case a single concentration is tested and compared to controls. These assays can also be used to assess the relative potency of a compound by testing a range of concentrations, in a range of 100 µM to 1 µM, for example, and computing the more efficient concentration.

The invention will be further illustrated by the following figures and examples. However, these examples and figures should not be interpreted in any way as limiting the scope of the present invention.

FIGURES

FIG. 1: Skin wound healing processes in virgin and pregnant female mice (A) Planimetry of wound area at each time point relative to original wound area (n=3). (B) Measurement of neoepidermal tongues and gaps (n=3). (C) Quantification of Ki67+ cells in epidermal wound edges (EpiD.) and the granulation demal tissues (D.) (n=3). (D) Quantification of the relative vessel surface per 20× field by fluorescence densitometry (n=3). (E) Quantification of the number of vessel type per 20× field (n=3). (F) Quantitative RT-PCR analysis of VEGF-A, VEGFR1, VEGFR2 mRNA expression normalized to mRNA GAPDH level (n=3), (G) Quantitative RT-PCR analysis of VEGF-C, VEGFR3 mRNA expression normalized to mRNA GAPDH level (n=3). T-test Student, * p<0.05; mean±SEM.

FIG. 2: Maternal wound activates FMCs and induces CCR2

Fetal cells quantification in bone marrow (A), blood (B) and skin/wound (C) after maternal skin injury (n=3). (D) PCR array analysis of cytokine and chemokine gene expression in FMCs sorted from maternal bone marrow in mice with or without wound at day 3 (n=6). White columns represent the ligand genes and the black columns represent the receptor genes. Quantitative RT-PCR analysis for CCR2 (E) and its ligand CCL2 (F) mRNA expression normalized to mRNA GAPDH level in normal skin and wound (n=3). (G) Quantitative RT-PCR analysis for CCL2 in sorted leukocytes from day 1 wound. T-test Student, * p<0.05; mean±SEM.

FIG. 3: CCL2 recruits FMCs to maternal wound and improve skin wound healing in pregnant mice 8 mm wound was performed on female mice pregnant with eGFP+ fetuses and the lesion was injected with CCL2 or PBS immediately after and 2 days after skin excision. (A) FACS analysis demonstrated significantly greater number of eGFP+ cells in wound of pregnant mice injected with CCL2 compare to mice injected with PBS (n=3). (B) Quantification of eGFP+ cells in wound at day 7 of PBS or CCL2 injected pregnant mice (n=3). (C) Quantification of eGFP+ cells in wound sections from pregnant mice with eGFP+ fetuses after PBS or CCL2 injection (n=5). (D) Planimetry of wound area at each time points relative to original wound surface (n=5). (E) Measurement of neo-epidermal tongues and gaps in wound sites (n=5). (F) Quantification of the relative vessel surface per 20× field by fluorescence densitometry (n=4). (G) Quantification of the number of vessel type per 20× field (n=4). (H) Quantification of vWF+ eGFP+ double positive vessel per 4× field (n=4). T-test Student, * p<0.05; mean±SEM.

FIG. 4: CCL2 recruits FMPCs to wound

Peripheral mononuclear blood cells (PBMCs) from female mice pregnant with eGFP$^+$ fetuses or virgin control mice with or without wound were collected at day 0, 1, 2, 3 and subjected to FACS analysis. (A, B and C) Percentage of CD11b$^+$ CD34$^+$ CD31$^+$ cells. Female mice pregnant with eGFP$^+$ fetuses were wounded and PBS or CCL2 were injected immediately after and 2 days after skin injury. PBMCs and wounds were collected 7 after for FACS analysis. (D) PBMC and (E) wound tissues were analyzed to determine maternal CD11b$^+$ CD34$^+$ CD31$^+$ myeloid progenitor cells (eGFP$^-$ gate) and fetal CD11b$^+$ CD34$^+$ CD31$^+$ myeloid progenitor cells (eGFP$^+$ gate) upon CCL2 or PBS administration. (D and E) Percentage of CD11b$^+$ CD34$^+$ CD31$^+$ cells in eGFP± gate (n=4). T-test Student, * p<0.05; mean±SEM.

FIG. 5: FMPCs express high percentage of CCR2 after maternal skin injury

Female mouse pregnant with eGFP$^+$ fetuses was wounded and eGFP$^+$ CD11b$^+$ CD34$^+$ CD31$^+$, FMPCs were isolated from blood at wound day 1 or female mouse CaG-eGFP was wounded and eGFP$^+$ CD11b$^+$ CD34$^+$ CD31$^+$, MPCs were isolated from blood at wound day 1. The recipient mouse was normal virgin female with the same genetic background as the donor mice. 1×10$^5$ FMPCs or MPCs were transplanted into the day 1 wound of the recipient mouse and the wound was harvested at day 7. (A) Quantification of CCR2$^+$/eGFP$^+$ cells in FMPCs or adult MPCs transplantation. (B) Quantification of CCR2$^+$/eGFP$^-$ in FMPCs or adult MPCs transplantation. (C) Quantification of CCR2+ cells in CD11b+ CD34+ CD31+ eGFP± gate (n=3).

Figure 6A:
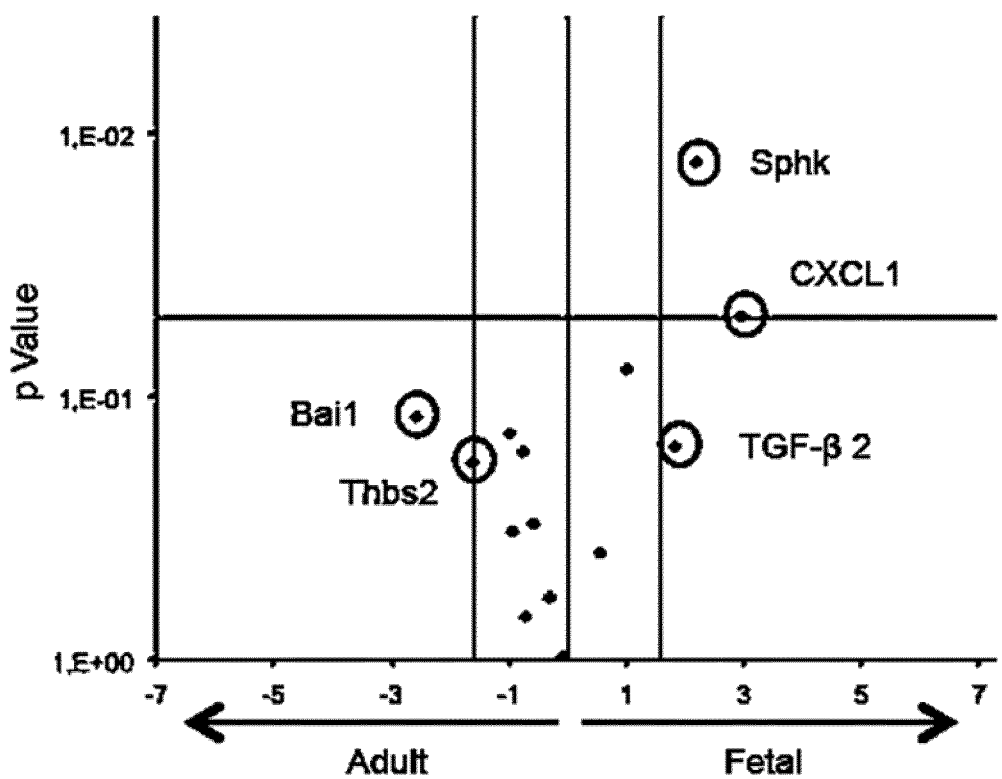

FIG. 6: FMPCs overexpress CXCL1 in wound

Female mouse pregnant with eGFP+ fetuses was wounded and eGFP+ CD11b+ CD34+ CD31+, FMPCs and eGFP− CD11b+ CD34+ CD31+, maternal MPCs were isolated from wound tissue at day 3. After mRNA extraction, high throughput PCR array analysis was performed. (A) Mouse PCR array analysis of angiogenesis-associated gene expression in FMPCs (right) and MPCs (left) (n=3). (B) Quantitative RT-PCR validation of CXCL1 mRNA expression normalized to mRNA GAPDH level (n=3).

FIG. 7: An 8 mm wound was created in pregnant female mice carrying eGFP+ fetuses. We injected Ccl2 or PBS into the wound immediately and two days after skin excision. (a) Planimetry of the wound area relative to the initial wound area, at various time points from $Ccr2^{KO/KO}$ virgin mice (n=5). (b) Planimetry of the wound area relative to the initial wound area, at various time points from $Ccr2^{KO/KO}$ female mice mated with $eGFP^{KI}$ $Ccr2^{KO}$ male mice (n=5). (c) Planimetry of the wound area relative to the initial wound area, at various time points (n=5) from $Ccr2^{KO/KO}$ female mice mated with eGFP male mice. (d) Quantifications of eGFP+ cells in sections of wounds from pregnant mice the injections of PBS or Ccl2 (n=3). Student's t-test, * $p<0.05$; mean±SEM.

FIG. 8: An 8 mm wound was created in 8 months old postpartum female SAD mice that had carried eGFP+ fetuses, or 8 months old virgin WT female mice. We injected Ccl2 or PBS into the wound immediately and two days after skin excision. (a) Planimetry of the wound area relative to the initial wound area, at various time points from 8 month old postpartum SAD mice (n=3). (b) Planimetry of the wound area relative to the initial wound area, at various time points from 8 months old virgin WT female mice (n=3). Student's t-test, * $p<0.05$; mean±SEM.

Figure 9:
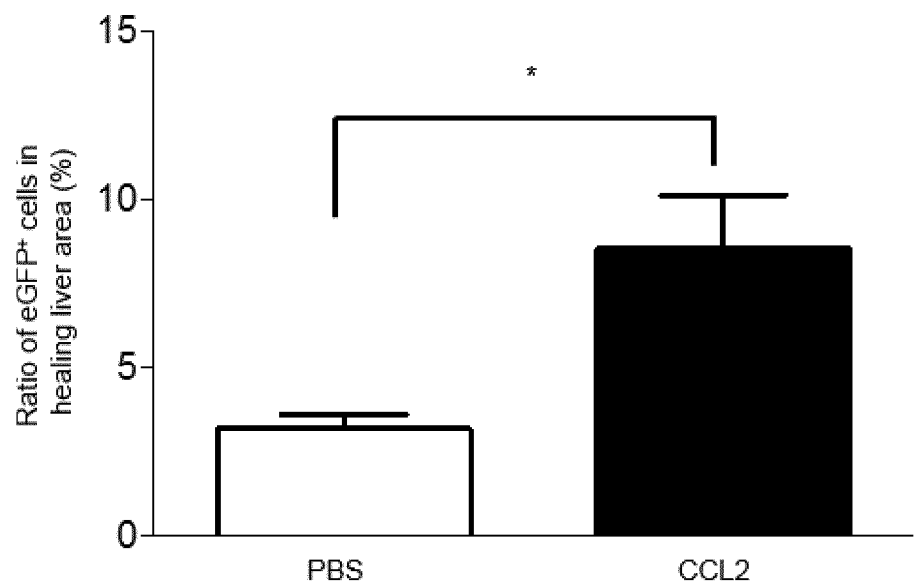

FIG. 9: Postpartum female mice that had carried eGFP+ fetuses received an hepatectomia. We injected Ccl2 or PBS into the damaged liver lobe. Mice were analyzed 7 days after the surgery. (a) Quantifications of eGFP+ cells in sections of liver from postpartum mice that received the injections of PBS or Ccl2 (n=3). Student's t-test, * $p<0.05$; mean±SEM.

FIG. 10: An 8 mm wound was created in virgin mice, pregnant mice or postpartum mice treated with clobetasol. We injected Ccl2 or PBS into the lesion immediately and two days after skin excision. Sirius red staining and quantification of collagen density (a) in virgin mice (n=3) (b) pregnant mice (n=3) and (c) postpartum mice treated with clobetasol (n=3). Scale bars: 50 μm. Quantitative RT-PCR analysis of Col1a, Col3a and TGFb mRNA levels normalized against GAPDH mRNA levels in the wound on day 7 in (d) virgin mice (n=3) (e) pregnant mice (n=3) and (f) postpartum mice treated with clobetasol (n=3).

EXAMPLE 1

Material & Methods

Mice: Male enhanced green fluorescence protein (eGFP) transgenic mice were obtained from Riken Laboratories (CD57BL/6-Tg (CAG-EGFP)lObs/J) and mated to Wild-type (WT) females on background C57BL/6 of 6-8 weeks old obtained from Harlan (Harlan). All mice care were in compliance with ethical rules of Université Pierre et Marie Curie (UPMC) animal care regulations.

Flow cytometry: Back skin was shaved and wounds were harvested, incubated overnight at 4° C. in 0.05% trypsin-EDTA (Invitrogen) for mechanical separation of the epidermis. The tissue were digested in Collagenase IV for 60 min at 37° C., vortexed every 10 min and filtered using a 100 μm cell strainer, followed by 40 μm cell strainer (BD Pharmingen) to obtain a single cell suspension. Blood were draw from the heart of the mice and the peripheral mononuclear blood cells were separated from erythrocytes and platelets using Ficoll 1.088 method (Health Care). After collected the ring, the cells suspension was washed with PBS (Life Technologies) and then filtered using a 40 μm cell strainer (BD Pharmingen). Antibodies used for cytometry were CD34-eFluor660 (1:100; eBioscience), CD11b-PERCP-Cy5.5 (1:100; eBioscience), CD31-PE-Cy7 (1:100; eBioscience), CCR2 (1:100; Santa Cruz) crossed with an anti-goat-alexa 555 (1:1, 1000 Invitrogen). Flow cytometry data was acquired using a BD LSRII (BD Pharmingen) and sorting were performed on a MoFlo cell sorter (Beckman Coulter), and subsequently analyzed with FlowJo software (Treestar, San Carlos, Calif.).

Immunostaining: We performed 5 μm cryosections from frozen tissue. After permeabilization with cold acetone, sections were blocked with 2% bovine serum albumin (BSA) (Sigma-Aldrich). Primary antibodies used including: rat anti-mouse CD31 (1:40; BD Biosciences), rabbit anti-mouse Lyve-1 (1:200; Abcam), rat anti-mouse F4/80 (1:250; Abcam), rat anti-mouse GR-1 (1:250; eBiosciences) rabbit anti-mouse Ki67 (1:200; Abcam), goat anti-mouse CCR2 (1:200; Santa Cruz biotechnology), goat anti-mouse CCL2 (1:200; Santa Cruz), rabbit anti-mouse Von Willebrand Factor (1:800; Abcam). For immunofluorescence, we used secondary antibodies goat anti-rabbit IgG labeled with Cy3 or Alexa 488, donkey anti-rat IgG labeled with Alexa 488 or Cy3 and rabbit anti-goat Alexa 555 (1:1000; Invitrogen). Slides were counterstained with 0.3 μg/ml DAPI (Sigma-Aldrich).

Microscopy, scoring and measurements: We used Nikon Eclipse 90i fluorescent microscope equipped with Nikon DS-Fil C digital camera (Nikon, Tokyo, Japan). For cell scoring, photographs of 3 different fields were taken, and labeled cells were counted by fluorescence densitometry and reported as percentage of total nuclei. Mean percentage of labeled cells was calculated for each specimen. Measurements were done using ImageJ software (NIH, Bethesda, Md.).

RNA extraction and quantitative PCR: Total RNA was extracted from cells or tissues using Trizol reagent as per the manufacturer's (Invitrogen) instructions and then reverse-transcribed with iScript cDNA synthesis kit (Bio-Rad). The resulting cDNA was used for PCR with the SYBR-Green Master PCR Mix (Roche). PCR and data collection were performed on a LightCycler 480 (Roche). The expression levels of samples were normalized to the housekeeping gene β-Actin.

Surgical wounds: Mice were anesthetized by inhalation of 4.9% isoflurane at 300 ml/min ambient air flow. After depilation, four 6 mm or one 8 mm surgical wounds were generated using punch biopsy devices. All tissues above the panniculus carnosus were excised. Wounds were left uncovered until they were harvested. Standardized pictures of the wounds were taken on different time points using a Sony Cybershot 10.1 megapixels DSC-W180 digital camera (Sony, Tokyo, Japan). Wound tissues were harvested either snap-frozen in liquid nitrogen or stored at −80° C.

Corticoïds treatment: 4 days after delivery, mice were treated with topical application on shaved dorsal skin of 200 μL of clobetasol (Dermoval) during 12 days.

Chemokine/Cells injection: After generated 8 mm wound, 100 μL of CCL2 (Clinisciences, Nanterre, France) was injected at day 0 and day 2 in the fourth cardinal points of the wound bed at a concentration of 0.5 ng·μL$^{-1}$. Or 10 000 cells were injected after FACS sorting resuspended into PBS using the same procedure at day 1.

PCR Array for Cytokines and Chemokines

The change in cytokine and chemokine expression was measured using RT$^2$ Profiler PCR Array for cytokines and chemokines system (Qiagen, Hilden, Germany). Total RNA was extracted from FACS isolated eGFP+ cells from bone marrow. Expression analysis of 86 cytokine and chemokine genes was performed Lightcycler 1536 system (Roche Diagnostics, Mannheim, Germany) according to the manufacturer's instructions. Data analysis was performed using the RT$^2$ Profiler PCR Array Data Analysis Template (Qiagen, Hilden, Germany). Data normalization was performed using five housekeeping genes (Actb, B2m, Gapdh, Gusb, Hsp90ab1) and the relative expression levels were calculated with $2^{-\Delta\Delta Ct}$.

PCR Arrays were performed in AP-HP Hopital La pitié Salpétrière ICM, using a LightCycler 1536 (Roche) with RT$^2$ Profiler PCR Arrays.

Statistical analysis: Statistical analysis was performed with the statistical software Graphpad Prism. Results were reported as mean±SEM. A single comparison between two groups was performed with an unpaired, two-tailed Student's t-test. Statistical significance of difference was defined when p-value was <0.05.

Results

Pregnancy Improve Skin Wound Healing by Enhancing Vascular Angiogenesis

Figure 1B:
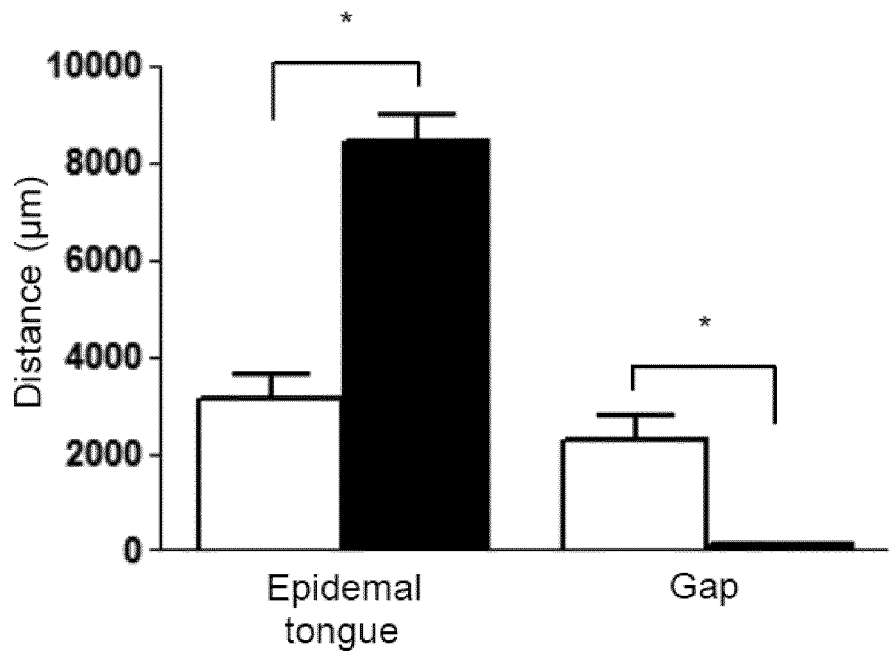
Figure 1C:
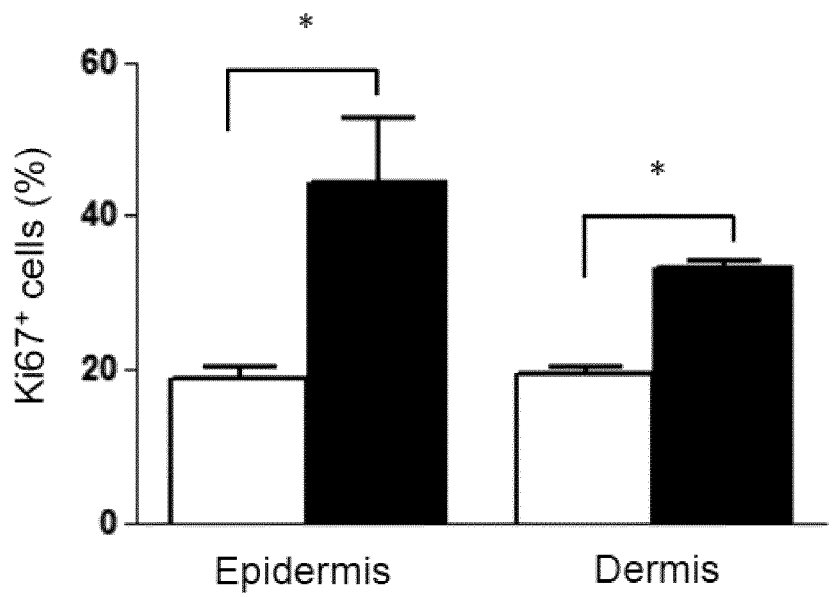

To evaluate whether pregnancy affects skin wound healing, we performed excisional wounds on dorsal skin of pregnant mice at gestation day 15.5 and their age matched respective virgin littermate. Wound closure was significantly accelerated in pregnant mice (mean wound surface on day 5: pregnant vs virgin=8.39% vs 13.67%; p=0.025) (FIG. 1A). Re-epithelialization, as measured by the length of the neo-epidermis covering the granulation tissue, was quicker in pregnant mice (FIG. 1B). Consistently, we also discovered increased number of Ki67$^+$ proliferating cells in both epidermis and dermis area of pregnant mice (FIG. 1C).

Figure 1D:
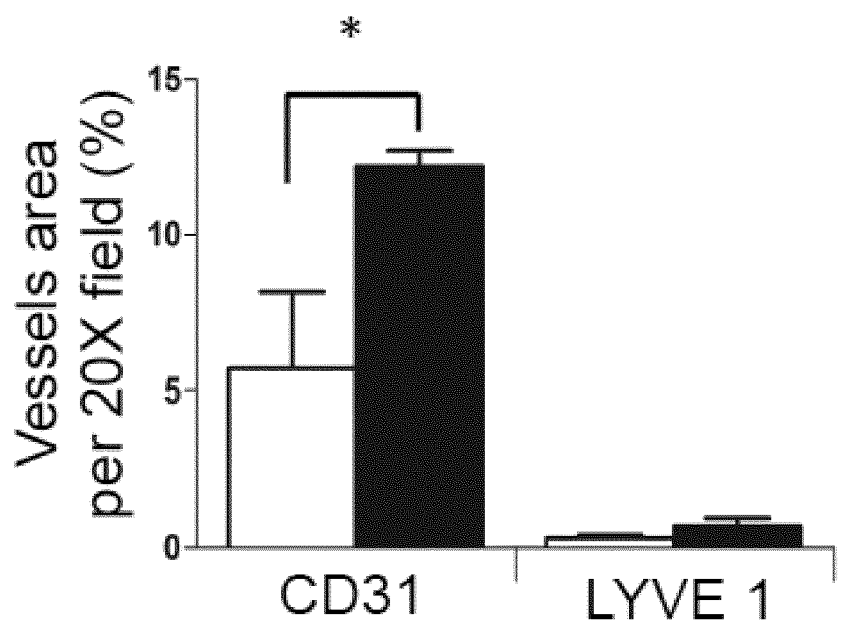
Figure 1E:
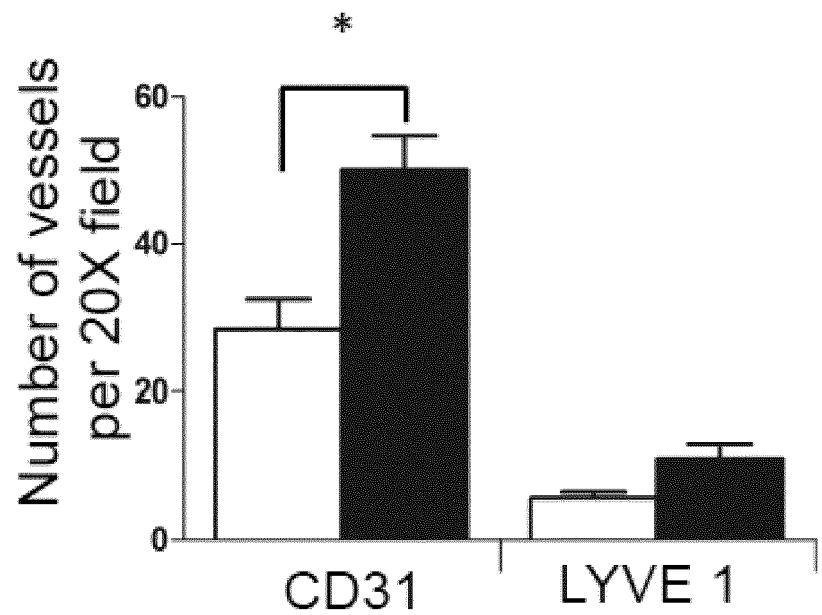
Figure 1F:
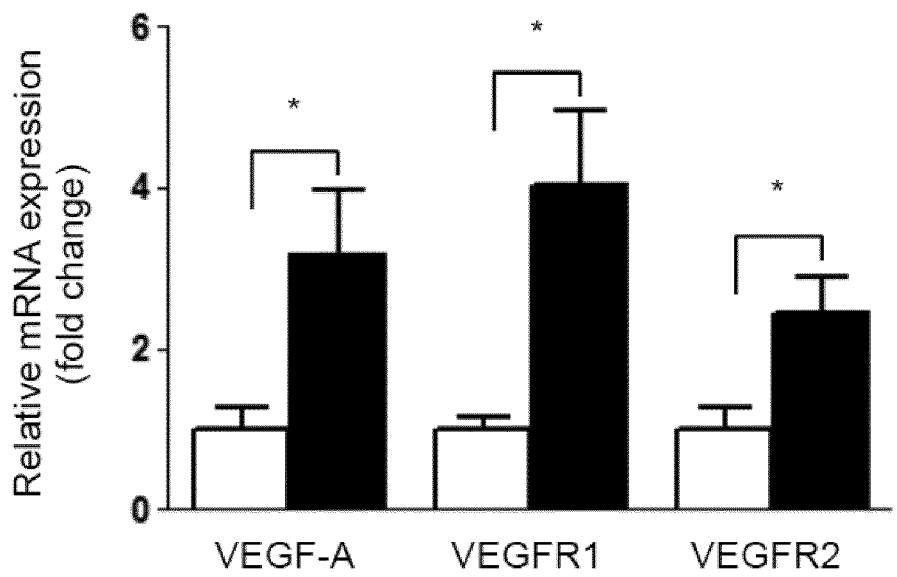
Figure 1G:
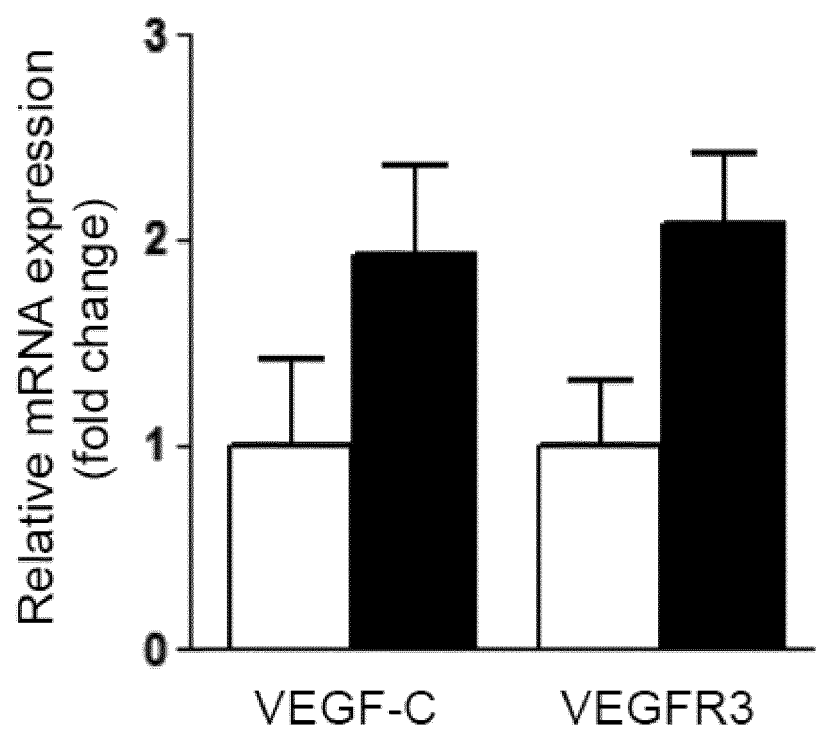

Inflammation and neovascularization are two crucial factors of wound healing process. Here we found CD31$^+$ blood vessel density within the wound bed increased in pregnant compared to virgin mice, while there were no difference of LYVE1$^+$ lymphatic vessel density between both groups (FIGS. 1D and 1E). VEGF-A binds to cell surface receptors VEGFR1 and VEFGR2 and mediates vascular angiogenesis, while VEGF-C acts on receptor VEGFR3 and promotes lymphatic angiogenesis. We discovered gene expression of VEGF-A, VEGFR1 and VEFGR2 were significantly elevated in wound sites of pregnant mice (FIG. 1F), however, VEGF-C and VEGFR3 levels were not altered (FIG. 1G). These results suggest that vascular, but not lymphatic angiogenesis, increased in pregnant wound.

Immunofluorescence analysis revealed no difference between pregnant and virgin mice in wound sites for infiltrating GR-1$^+$ neutrophils, and F4/80$^+$ macrophages, thus suggest inflammation appears to be unchanged in pregnant wound (Data not shown).

Taken together, these results provided initial indication that pregnancy improves maternal skin wound healing by enhancing vascular angiogenesis.

Maternal Skin Wound Activates FMCs by Inducing CCR2

Our laboratory previously reported that FMCs actively participates in maternal wound healing and VEGF-A plays a crucial role in recruiting these cells. To further investigate the role of fetal cells in maternal wound healing, we mated virgin C57BL/6 females with heterozygous enhanced green fluorescence protein (eGFP) males, and performed excisional wounds on dorsal skin at 15.5 day of pregnancy (Data not shown). The FMCs were identified by their expression of eGFP and quantified by fluorescence-activated cell sorting (FACS) from maternal organs. We found that fetal cell dramatically increased 1 days after wound in bone marrow (FIG. 2A), blood (FIG. 2B) and wound (FIG. 2C), and restored to normal level at day 3, thus indicates that fetal cells activation is an early and transient process.

In order to identify novel targets, especially chemokines, which are activated by maternal skin wound in FMCs, we performed PCR array analysis on sorted fetal cells from bone marrow with or without skin injury. CCR2 was the most significantly upregulated chemokine receptor after injury (FIG. 2D), thus indicated that maternal wound may induce CCR2 in FMCs.

Moreover, eGFP$^+$ FMCs were detected in wound tissue and a considerable portion of these cells expressed CCR2 (Data not shown). Furthermore, in peripheral blood, only 1.5% of eGFP$^+$ FMCs expressing functional CCR2 in unwounded mice. However, 90% of these cells expressed CCR2 one day after skin injury, while 20% of them still expressing CCR2 at day 3 (Data not shown). Collectively, these results suggest that early post-wound activation of CCR2 signaling in fetal cells could serve to trigger FMCs from circulation blood to wound site.

Figure 2A:
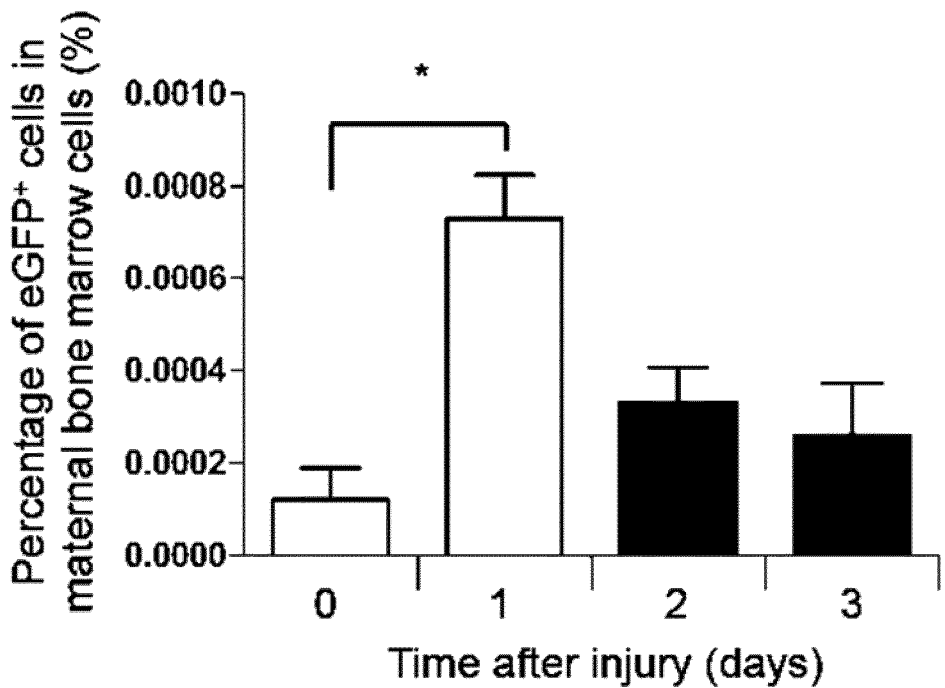
Figure 2B:
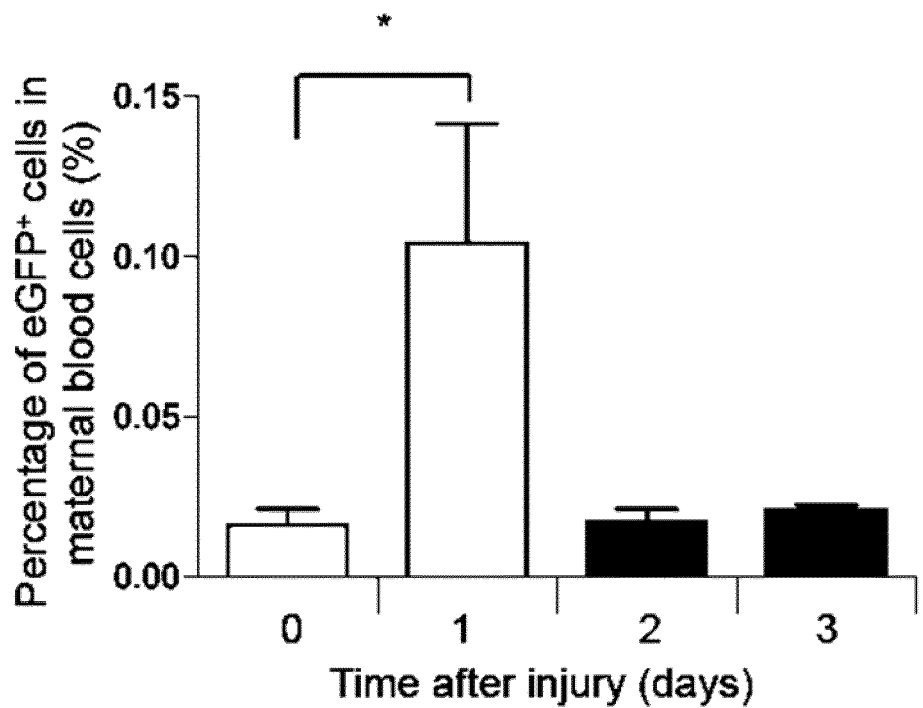
Figure 2C:
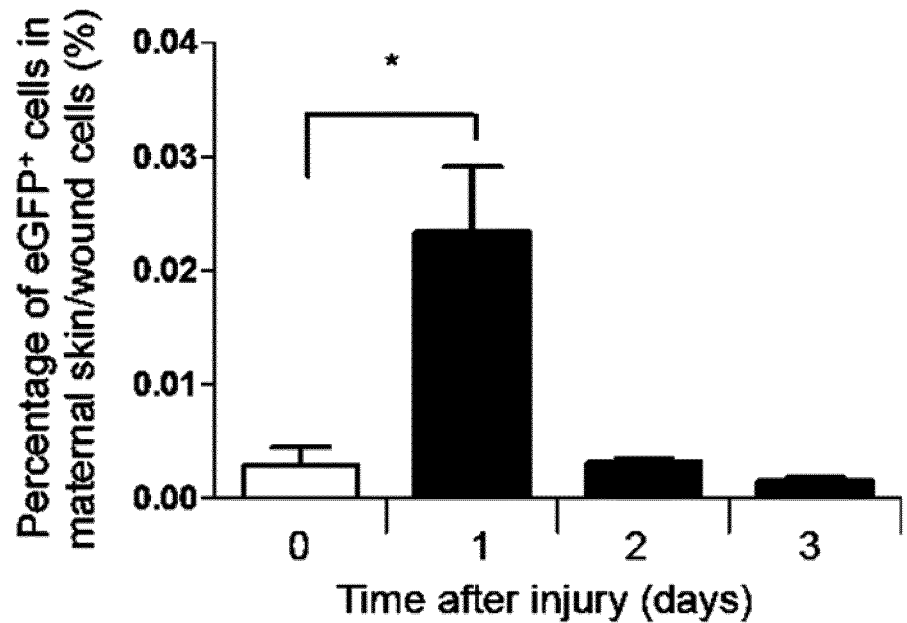
Figure 2D:
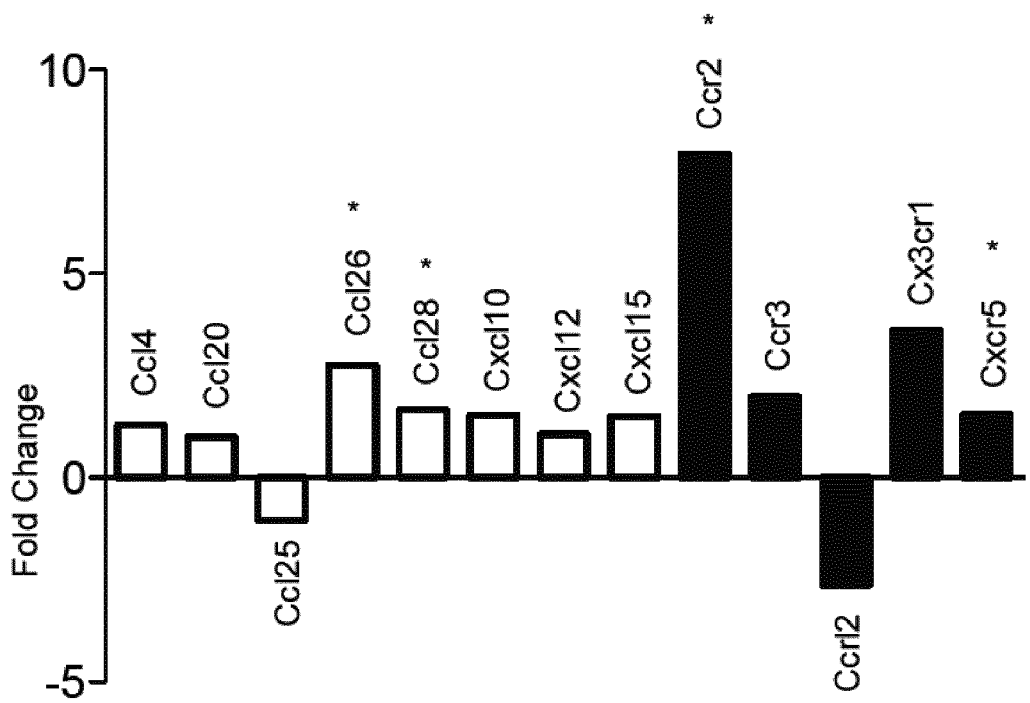
Figure 2E:
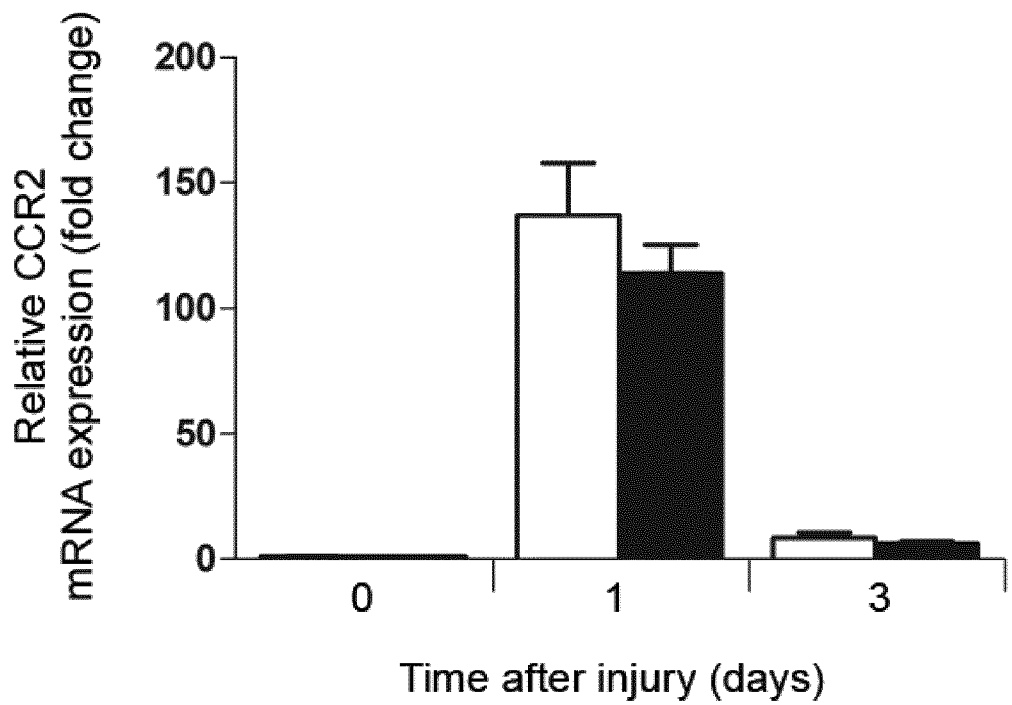
Figure 2F:
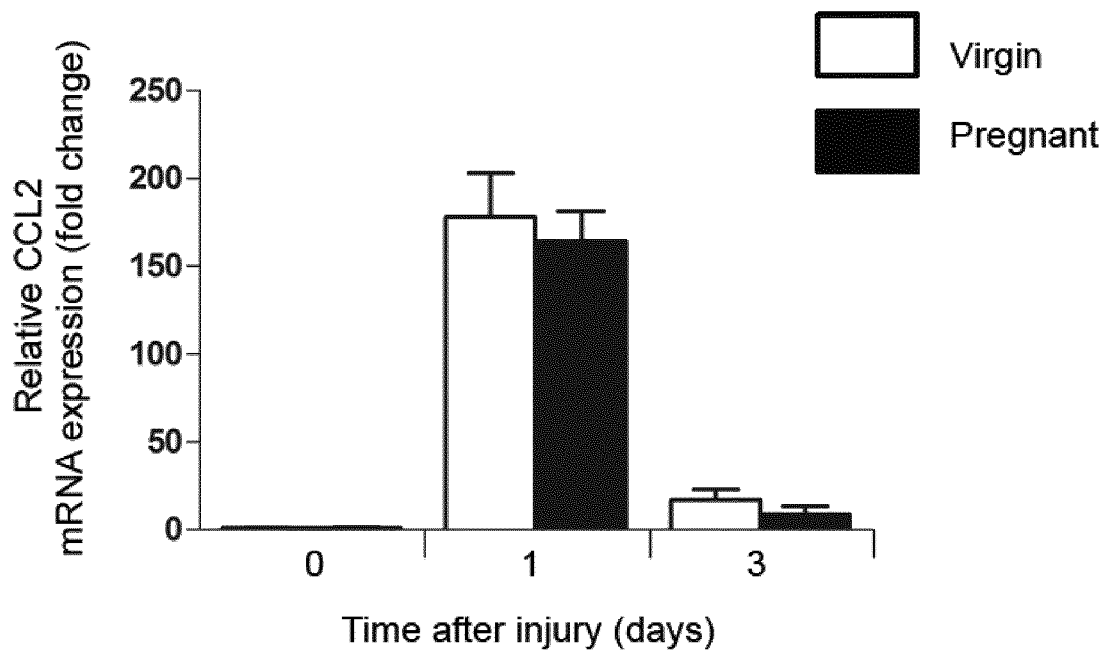

Overexpression of CCL2/CCR2 During Early Skin Wound Healing is not Affected by Pregnancy To further determine CCR2 chemotactic cues in wound and which ligand of CCR2 is triggering the movement of FMCs to injured skin, we measured the expression of CCR2 and its two major ligands CCL2 and CCL8 at skin wound bed of pregnant and virgin mice. CCR2 mRNA dramatically increased one day after injury and significantly decreased at day 3 from the level of day 1 (FIG. 2E), therefore suggests that CCR2 overexpression in injured skin is an early and transient event. Correspondingly, protein level of CCR2 follows the same pattern as its mRNA (Data no shown). Interestingly, one of the CCR2 ligand, CCL2 level is in parallel to CCR2 expression, with strong increased at day 1 and dropped at day 3 (FIG. 2F). Meanwhile, the other CCR2 ligand, CCL8 expression only have slight increase at day 1 and significantly increased at day 3 (Data not shown). These data indicate that CCL2/CCR2 signaling is specifically overexpressed early during wound healing. In addition, the mRNA level of CCR2, CCL2 and CCL8 in wound tissue have no difference between virgin and pregnant mice (FIG. 2E, 2F and supplemental figure not shown) indicate that pregnancy does not affect this signaling pathway.

Figure 2G:
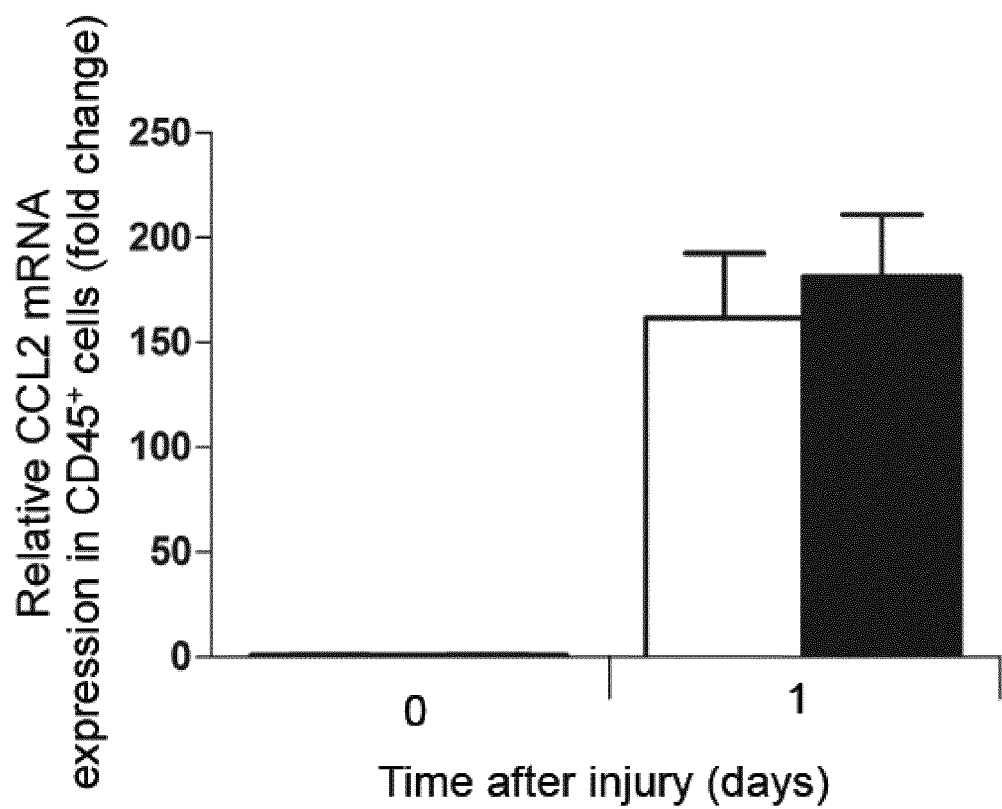

To further identify the specific cell types secreting CCL2, we sorted CD45$^+$ leucocytes from normal skin and day 1 wound, and discovered robust overexpression of CCL2 in wound, thus suggest immunocytes' secretion of CCL2 during early wound healing process (FIG. 2G and supplemental figure not shown). Co-immunofluorescent analysis demonstrated that F4/80$^+$ monocytes, not GR-1$^+$ neutrophils, expressed CCL2 (data not shown), therefore suggest resident monocytes secret initially CCL2. In addition, CCL2 were also detected in CD31$^+$ endothelial cells (data not shown). Moreover pregnancy does not affected early inflammation (data not shown) and the secretion of CCL2 (FIG. 2G).

Collectively, these data suggested that monocytes and endothelial cells secrete CCL2 during initial stage of skin wound healing, and not affected by pregnancy.

CCL2 Recruits FMCs to Maternal Wound

Figure 3A:
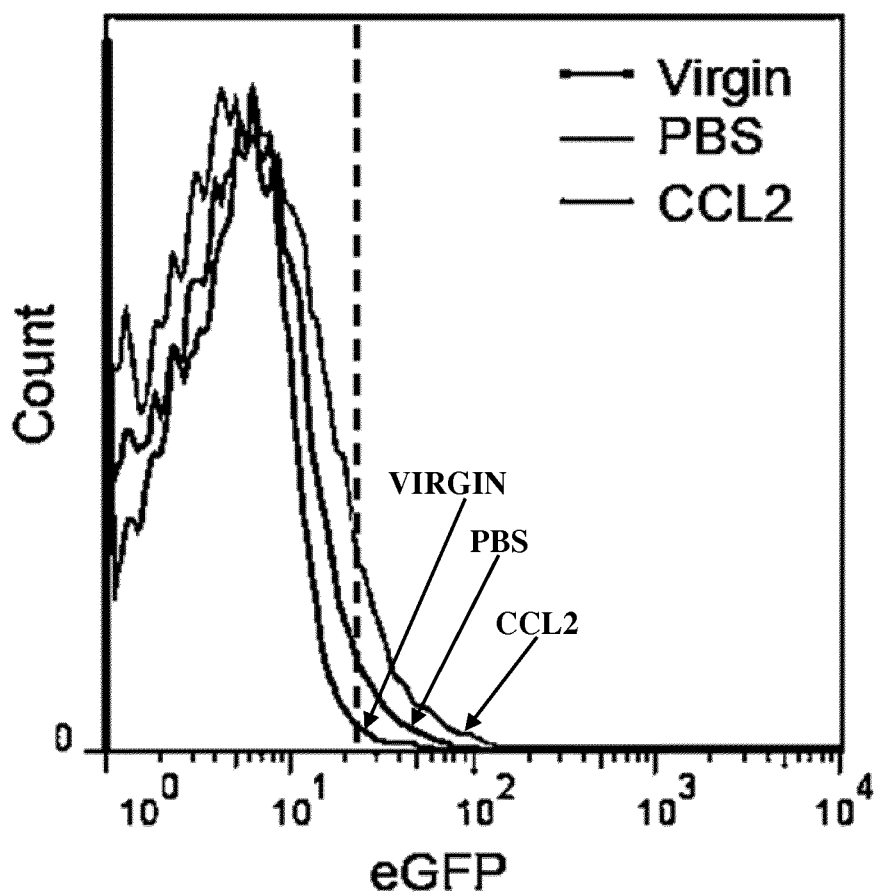
Figure 3B:
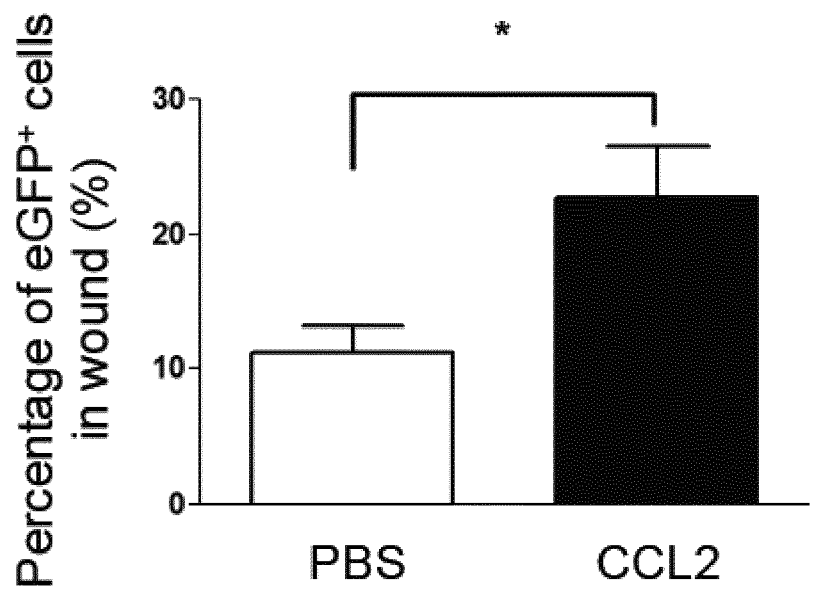
Figure 3C:
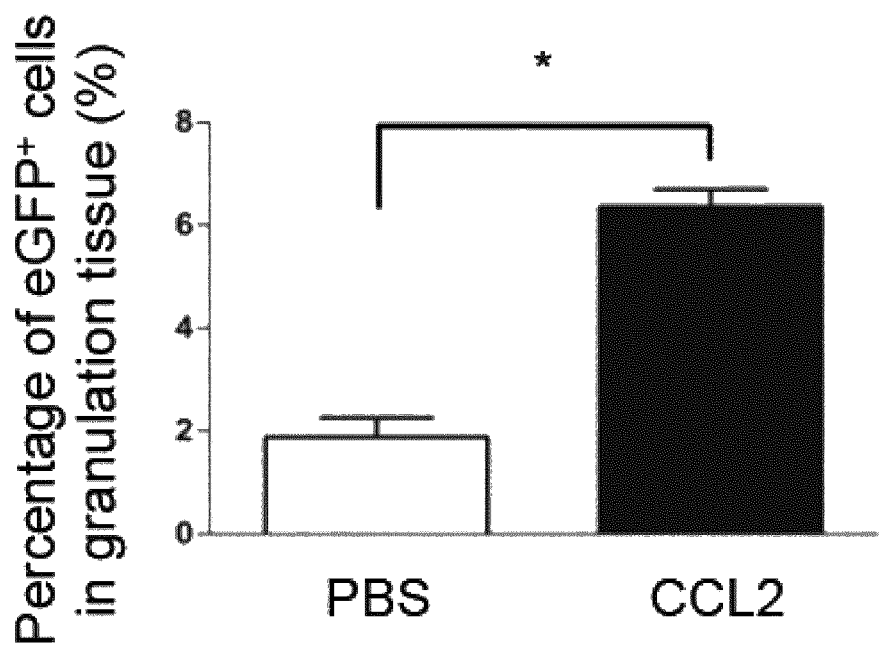

FMCs are able to infiltrate into the maternal wound and participate in the healing process. Due to the high percentage of FMCs expressing CCR2 on their surface and overexpression of CCL2 in wound tissue during early stage of healing, we speculated that CCL2 may mediates the early recruitment of FMCs to wound. To attest this hypothesis, we injected recombinant CCL2 mouse protein or PBS as control into the wound bed at day 0 and day 2 after excisional wounds. We initially quantified eGFP$^+$ cells number in blood and skin wound of pregnant mice injected with CCL2 or PBS using FACS analysis at day 7. In blood, the eGFP$^+$ cell number wasn't different between the mice injected with CCL2 and PBS (data not shown). Interestingly, skin wound tissue injected with CCL2 contained more than double number of eGFP$^+$ cells than PBS (FIGS. 3A and B). In order to confirm this finding, we performed immunofluorescence analysis on skin wound granulation tissue at day 7. In accordance with our FACS results, the number of eGFP$^+$ cells was almost three times more in the sections of CCL2 injected mice in compare with PBS injected mice (FIG. 3C). Together, the results suggest CCL2-CCR2 pathway mediated signals mediates the recruitment of FMCs to wound sites.

Figure 3D:
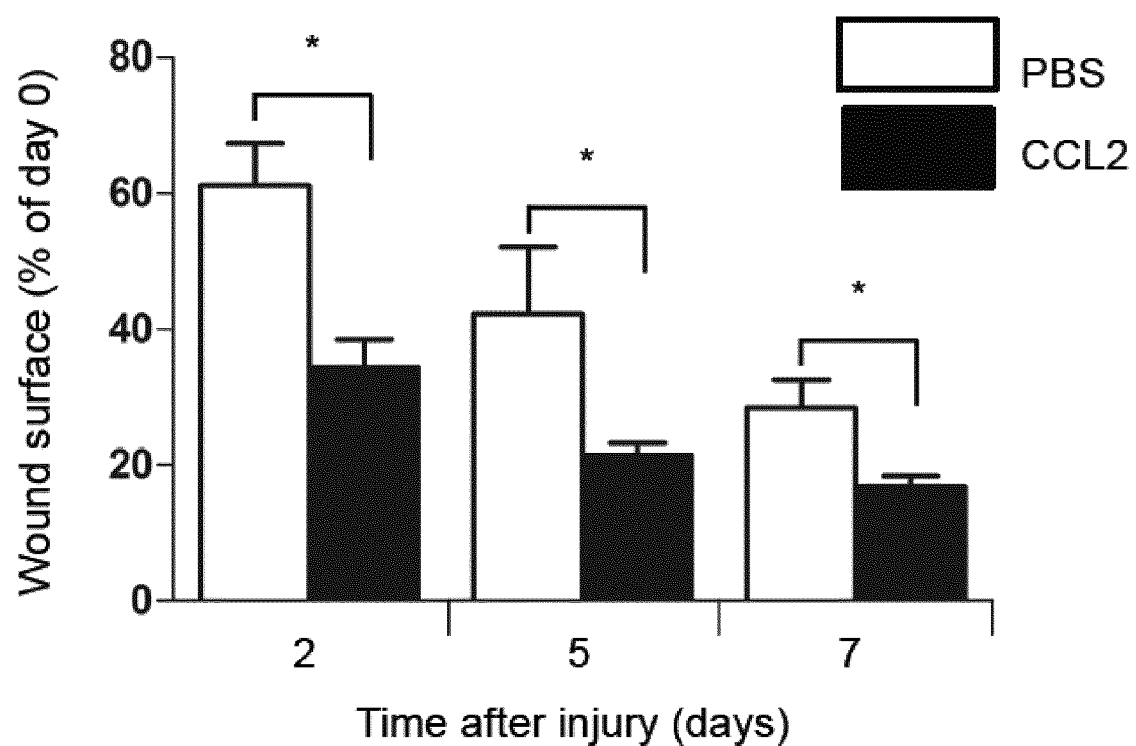
Figure 3E:
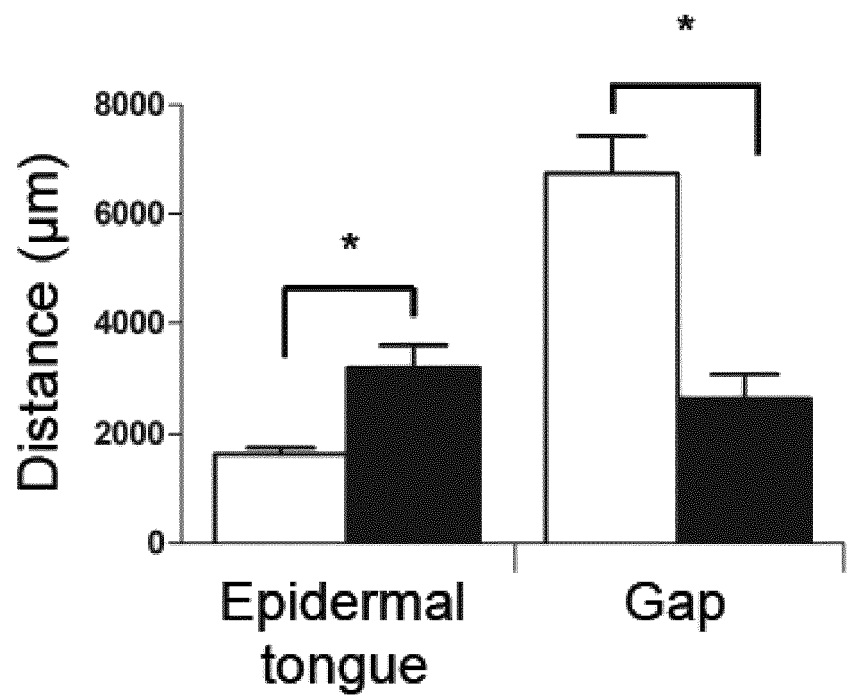
Figure 3F:
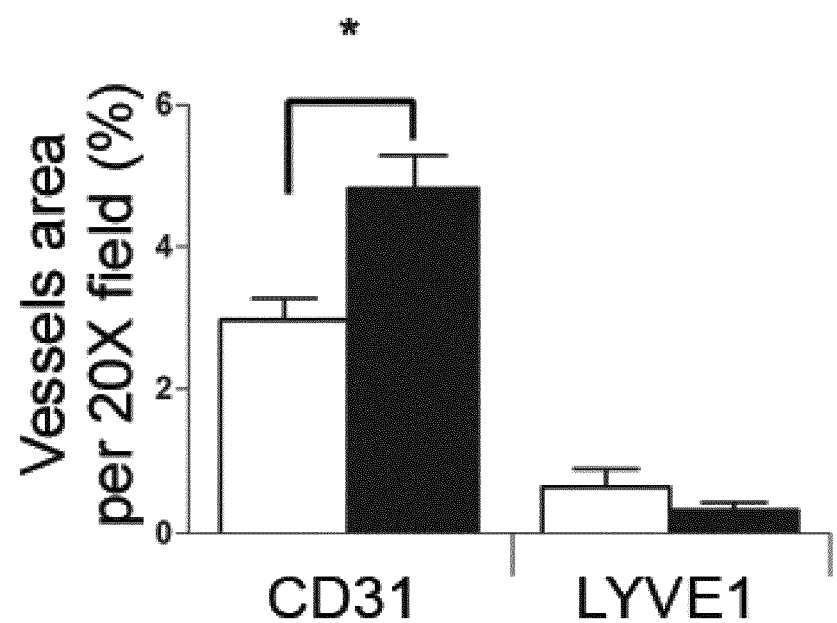
Figure 3G:
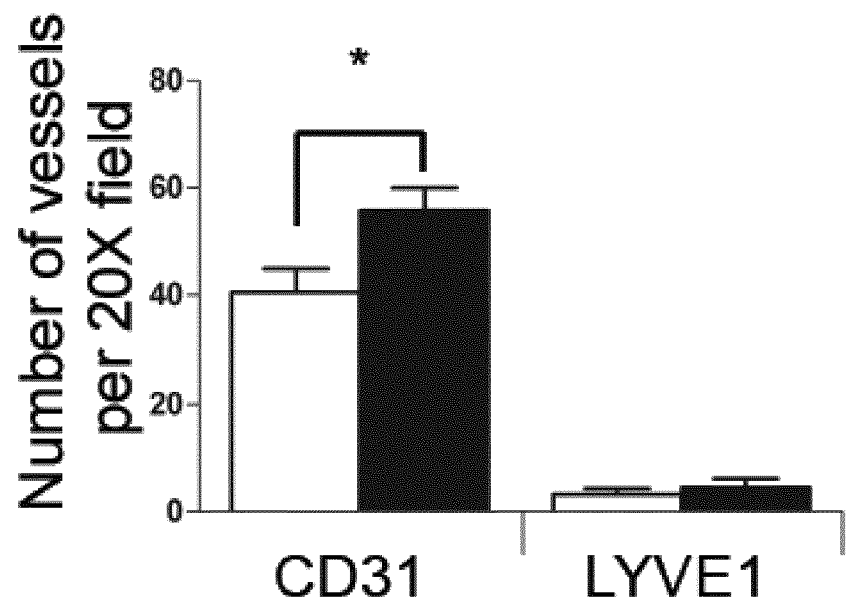
Figure 3H:
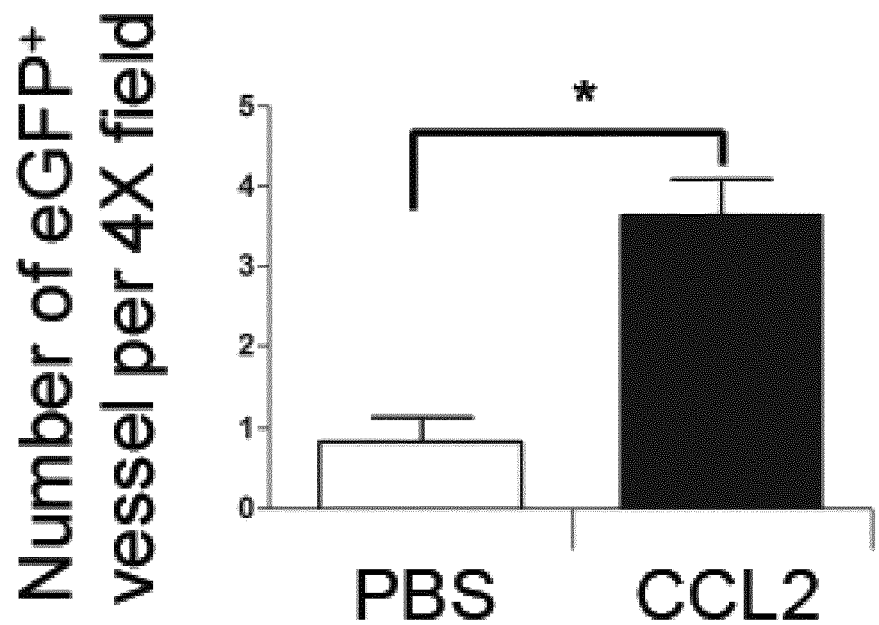

CCL2 Administration Improves Wound Healing by Enhancing Neovascularization in Pregnant but not in Virgin Mice FMCs participate in inflammation and angiogenesis during maternal wound healing. Here, we also demonstrated that CCL2 recruits FMCs to wound (FIG. 3A-C). Therefore, we further analyzed the maternal wound healing process upon CCL2. For the mice injected with CCL2, injured surfaces reduced to less than 16.8% (FIG. 3D), meanwhile for mice injected with PBS, wound areas remained over 28.4% of the original lesion at day 7 after skin excision (p=0.024) (FIG. 3D). Concomitantly, neo-epidermal tongue measurements on tissue sections, showed increased re-epithelialization after CCL2 injections (FIG. 3E). Moreover, proliferation as measured by the number of Ki67$^+$ cells, was elevated in both epidermis and dermis area of CCL2 injected mice (data not shown). Neovascularization as measured by CD31$^+$ blood vessel density as well as VEGF-A, VEGFR1 and VEGFR2 gene expression were significantly elevated in wound site of CCL2 injected mice (FIGS. 3F and 3G and data not shown). On the contrary, lymphatic angiogenesis was not altered upon CCL2 administration (FIGS. 3F and 3G, and data not shown). In addition, inflammation in the wound, as measured by the number of GR-1$^+$ and F4/80$^+$ cells in granulation tissue demonstrated no difference between CCL2 and PBS injected mice (data not shown). Nassar et al. reported that FMCs form blood vessel in maternal wound. Consistently, we also identified Von Willebrand Factor (vWF) positive blood vessels largely, at least partially, comprised of eGFP$^+$ FMCs, and the number of these fetal microchimeric vessels was significantly higher in CCL2 injected compared to PBS injected mice (FIG. 3H). We concluded from these data that CCL2 improve healing by promoting maternal neovascularization and formed fetal origin vessels.

To further determine whether CCL2 improves skin healing through the effect of FMCs or directly affect wound closure, we analyzed the wound healing upon CCL2 administration in virgin mice. Strikingly, for virgin mice, CCL2 injection did not change the healing for all paradigms compared to PBS injection: wound surface, neo-epidermal tongue, proliferation, inflammation, angiogenesis and lymphangiogenesis (data not shown). Therefore the effect of CCL2 on improving wound healing is limited to pregnant, not virgin mice, thus extended our argument that CCL2-recruited FMCs contributed to promoting maternal neovascularization and improving wound healing.

Overall, these data suggested that CCL2's effect on healing is through fetal cells.

A Specific Subpopulation of FMCs Respond to CCL2 in Maternal Wound Healing

Figure 4A:
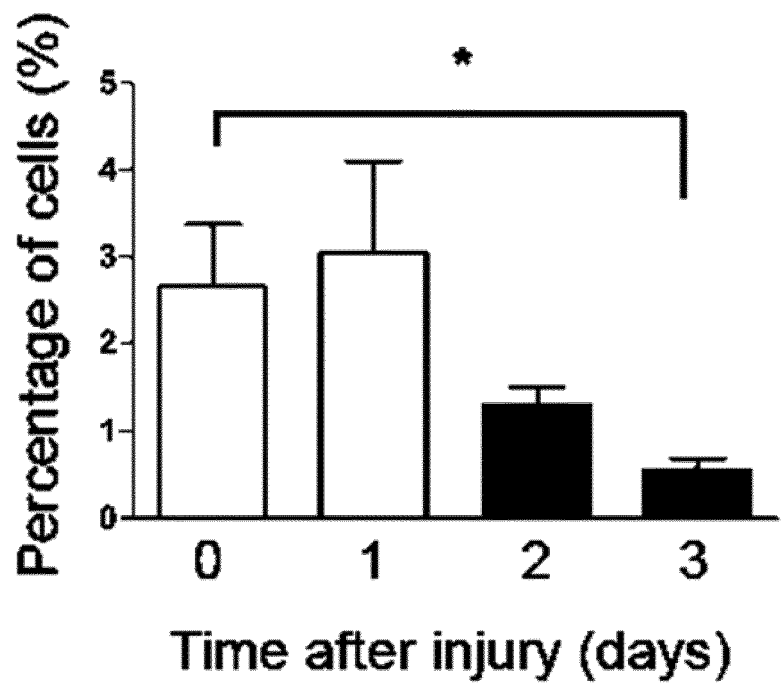
Figure 4B:
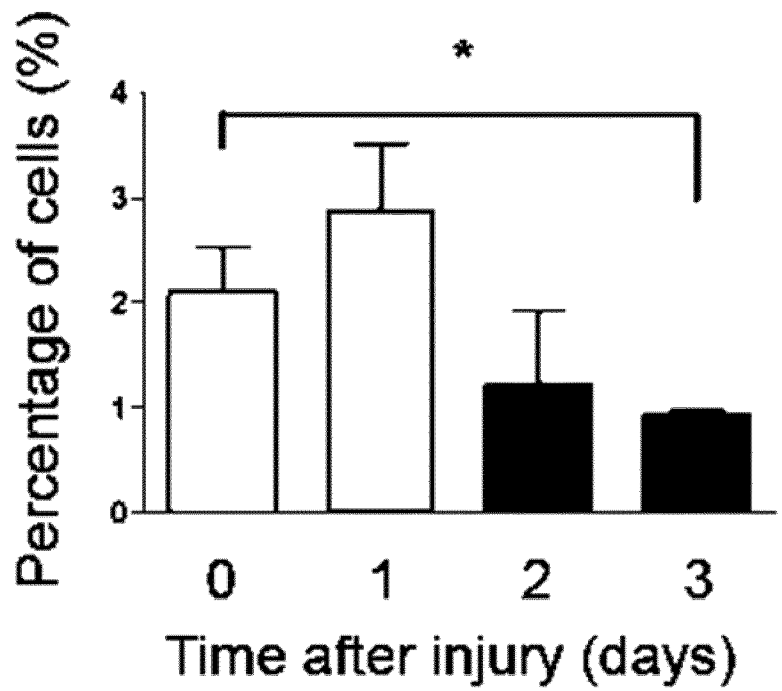
Figure 4C:
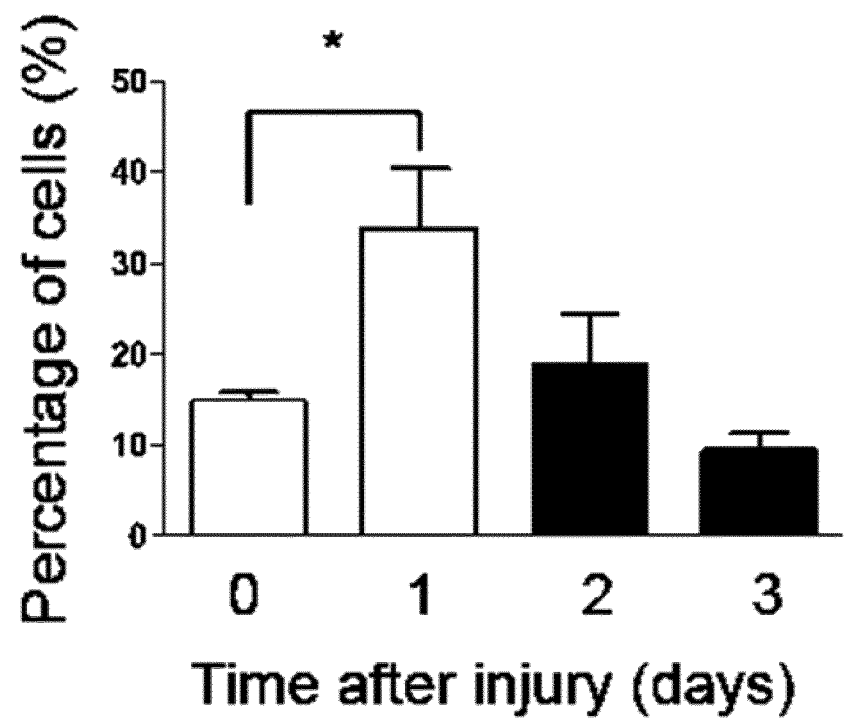

Maternal wound recruits fetal myeloid progenitors (FMPCs) and fetal endothelial progenitors (FEPCs). Here, we further investigated the dynamics of MPCs and EPCs in peripheral blood during wound healing. In virgin control, the number of MPCs, defined as CD11b$^+$ CD34$^+$ CD31$^+$, maintained at the same level as unwound condition during the first two days, and significantly decreased at day 3 after wound (FIG. 4A). In pregnant mice, the number of maternal MPCs, defined as eGFP$^-$ CD11b$^+$ CD34$^+$ CD31$^+$, displayed the same pattern as the virgin MPCs (FIG. 4B). On the contrary, the number of FMPCs, defined as eGFP$^+$ CD11b$^+$ CD34$^+$ CD31$^+$, markedly elevated at day 1 post wound compares to unwound condition. For day 2 and day 3, although reduced from day 1, FMPC number still maintained the same level as unwound (FIG. 4C). EPCs are well recognize as a crucial factor for neovascularization in wound healing process. Here we also studied the pattern of maternal (eGFP$^-$) and fetal (eGFP$^+$) EPCs defined as CD11b$^-$ CD34$^+$ CD31$^+$. Both populations displayed a delayed and abrupt increase at day 3 after skin lesion (data not shown). Collectively, these observations demonstrated that: unlike maternal MPCs, FMPCs elevated during early healing process, while maternal and fetal EPCs share parallel pattern. Thus, FMPCs are specifically activated after wound.

Figure 4D:
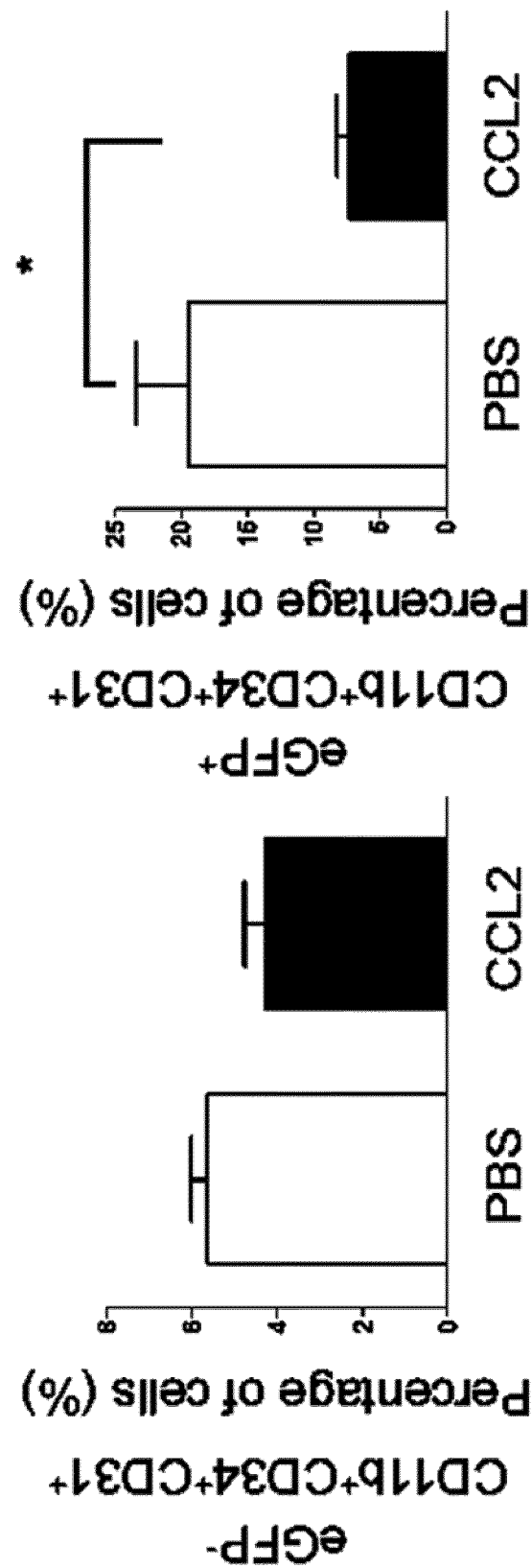
Figure 4E:
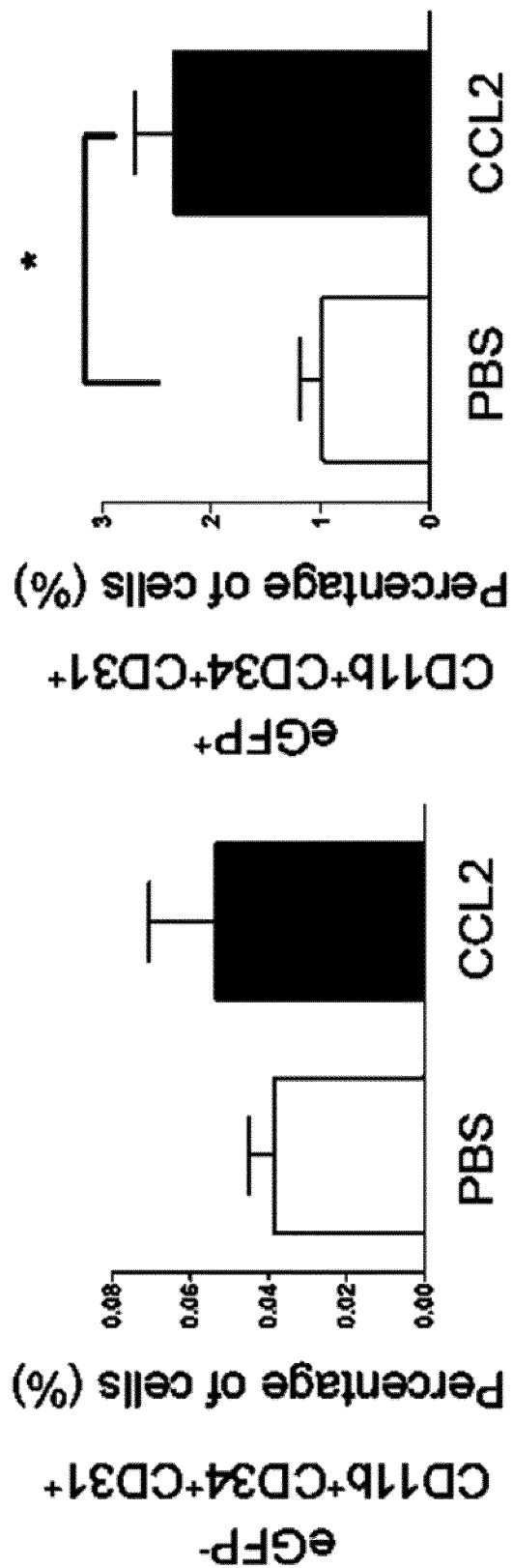

We further investigated this fetal specific population of MPCs response to CCL2 administration. The number of FMPCs was significantly decreased in peripheral blood (FIG. 4D) and markedly increased in the wound tissue of mice injected with CCL2 (FIG. 4E). Meanwhile, the number of maternal MPCs was not change upon CCL2 injection in both blood and wound tissue (FIGS. 4D and 4E). Furthermore, both maternal and fetal EPCs numbers detected in blood and wound were same between CCL2 and PBS injection (data not shown). Collectively, these results suggest that CCL2 specifically recruits FMPCs from blood to wound during the healing process.

FMPCs Organize Blood Vessel Endothelium in Wound

To assess the cellular lineage of FMPCs in vivo, we isolated this population from the peripheral blood of mice pregnant with eGFP$^+$ fetuses at wound day 1. As control eGFP$^+$ adult MPCs were isolated from peripheral blood of virgin heterozygous eGFP+ female mouse. The cells were injected into the day 1 wound site of a eGFP$^-$ wild type BL/6 virgin mouse. Immunofluorescence analysis was utilized to observe the wound tissue section of the recipient mice at wound day 7. eGFP$^+$ FMPCs displayed vWF$^+$ endothelial phenotype. We even discovered blood vessels largely comprise of eGFP$^+$ vWF$^+$ FMPCs, with confocal microscopy confirming the intimal position of eGFP$^+$ cells in vessel (data not shown). eGFP$^+$ FMPCs also expressed marker of smooth muscle cell (α-SMA), but not marker of macrophage (F4/80) (data not shown). On the contrary, eGFP$^+$ adult MPCs did not express endothelial marker vWF and myofibroblast marker α-SMA (data not shown). These results suggest that FMPCs differentiate into endothelial and myofibroblast lineage in wound.

FMPCs Form Proliferative Cluster and Express High Percentage of CCR2

Figure 5A:
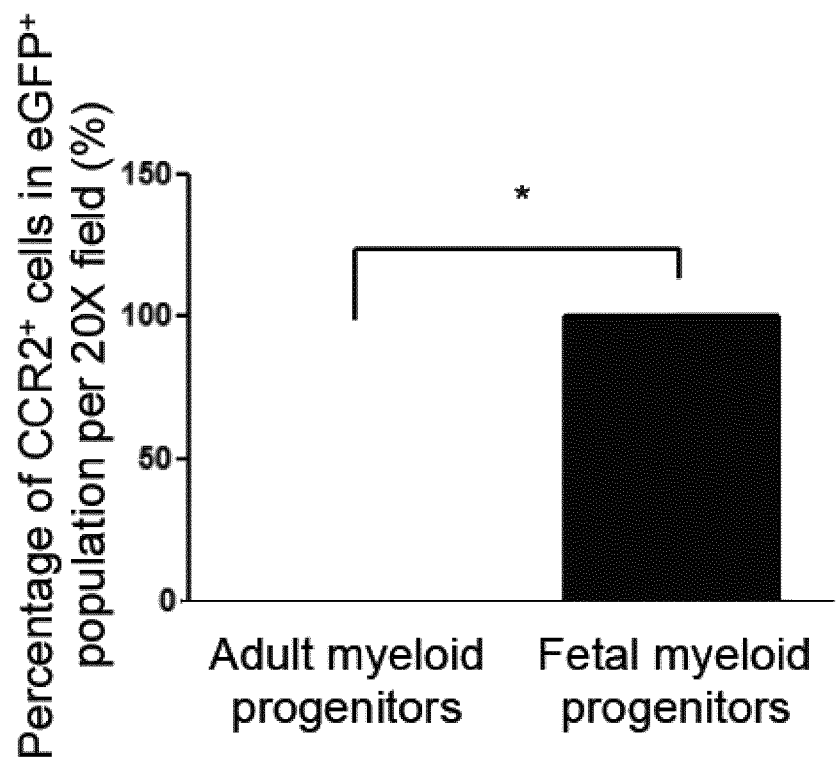
Figure 5B:
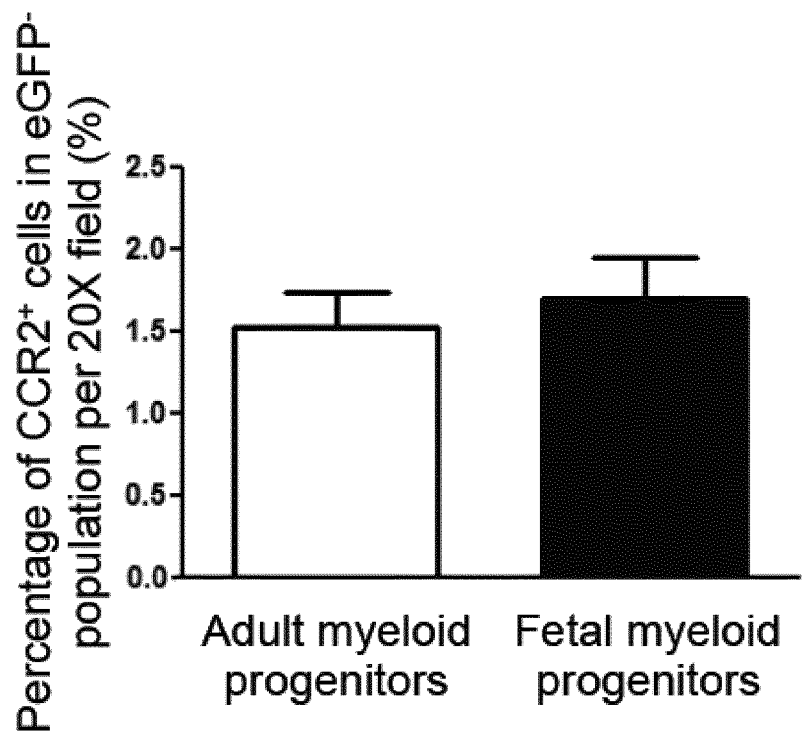
Figure 5C:
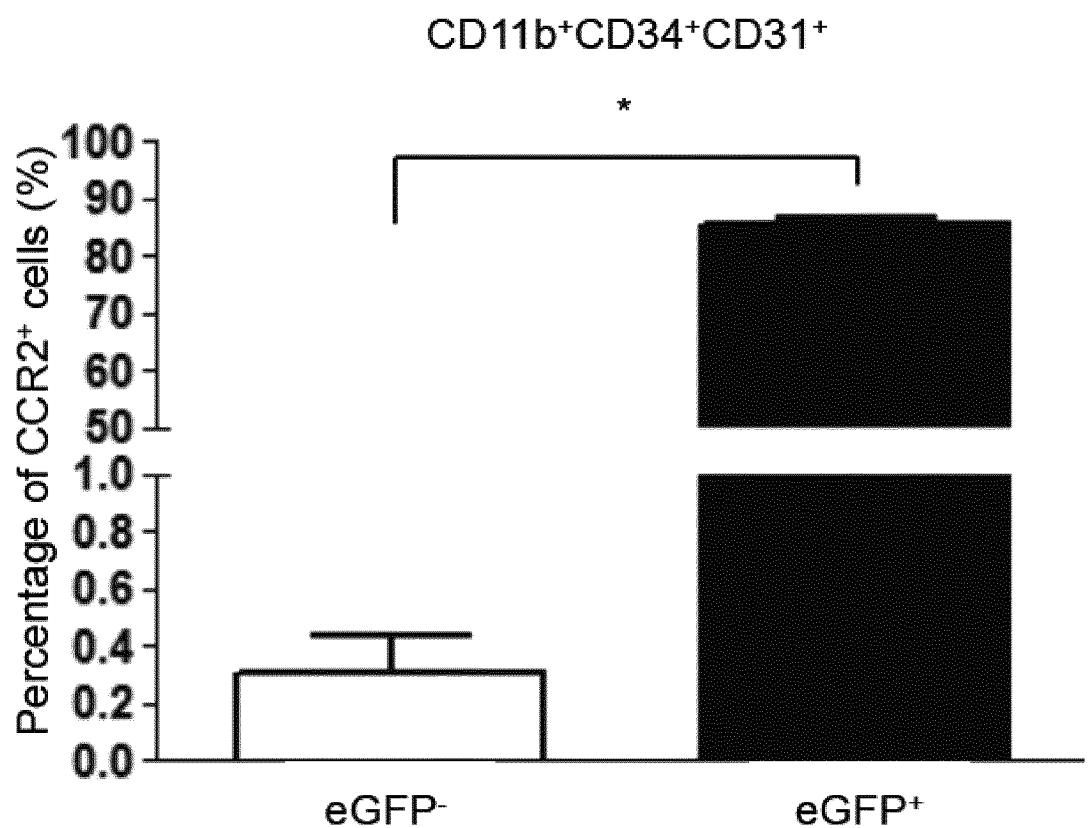

Unlike adult MPCs, which maintain isolated single-cell form, FMPCs formed proliferative cluster and stained positive for Ki67 (data not shown). Interestingly, immunofluorescence analysis demonstrated that FMPCs detected in skin wound site, expressed high percentage of CCR2 (data not shown), lead us to speculate that CCL2/CCR2 interactions guide the recruitment of FMPCs into wound tissue. Indeed, in situ, almost all of FMPCs, but none of the adult MPCs expressed CCR2 (FIG. 5A). Meanwhile, the percentage of CCR2 expressing non eGFP cells was almost identical between FMPCs and adult MPCs injected samples (FIG. 5B). Furthermore, FACS analysis was performed on blood of mice pregnant with eGFP$^+$ fetuses at wound day 1. CCR2 was expressed by about 90% of FMPCs and by only 0.3% of maternal MPCs (FIG. 5C). Collectively, these results suggest that CCR2 mediate the recruitment of FMPCs from blood to wound site.

FMPCs Overexpressed CXCL1 in Wound

Figure 6B:
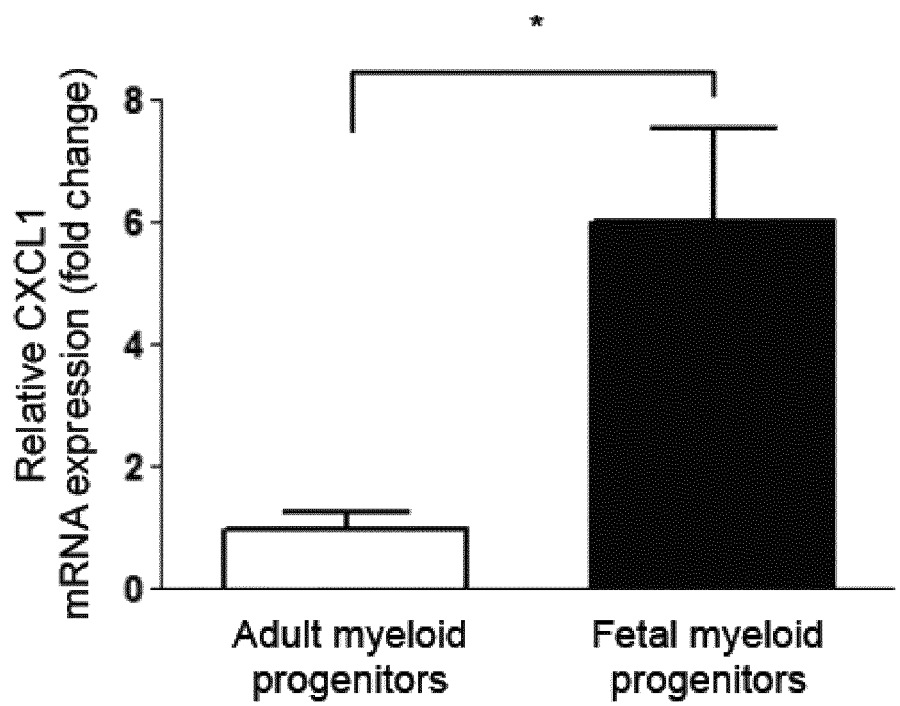

To investigate the potential paracrine effects of FMPCs on angiogenesis, we sorted eGFP$^+$ FMPCs and eGFP$^-$ maternal MPCs from the wounded skin tissue of mice pregnant with eGFP$^+$ fetuses at day 3. Angiogenesis stage of skin wound healing occurs at day 2-3, angiogenetic factors secretion as well as recruitment of EPCs reach maximum at day 3-4. Here, we studied the gene expression profile of angiogenesis factors at day 3 using mouse angiogenesis PCR array analysis, and the prevalent transcripts were plotted in FIG. 6A. The most upregulated genes include CXCL1, Sphk and TGF-β2, with chemokine CXCL1 being the highest increased transcript. On the other hand, certain angiogenesis inhibitor genes were downregulated, namely Thbs2 and Bai1. FIG. 6B shows quantitative RT-PCR analysis validation of CXCL1 expression, which again demonstrated almost six fold higher CXCL1 mRNA level in FMPCs than in maternal MPCs. Finally, we performed immunofluorescence analysis on sections of wounds injected with eGFP+ FMPCs or eGFP+ adult MPCs, and discovered only FMPCs overexpressed CXCL1 (data not shown). These results suggest FMPCs secret pro-angiogenesis factors, especially CXCL1, to enhance maternal angiogenesis.

CCL2 Improves Delayed Wound Healing in Postpartum Mice (Data not Shown)

Fetal cells have been reported transferred into maternal circulation during pregnancy and engrafted in maternal bone marrow postpartum, even throughout life. Corticoids can delay skin repair, therefore clobetasol administration has been recognized as chronic wound healing model in mice. Here, to evaluate the effect of CCL2 in a of delay wound healing model for postpartum situation, we mated virgin females with heterozygous eGFP transgenic males. 2 weeks after delivery, females mice which gave birth to eGFP$^+$ pups received daily topical application of dermoval (clobetasol cream) on the lower back for 14 days to induce skin atrophy. Then excisional skin injury was performed on dermoval treated area, and CCL2 or PBS was injected at day 0 and day 2 post wound. Pre-wound clobetasol application effectively prolong the normal healing process with wound surface at day 7 maintained at 100% of original lesion in compare to normal healing process for 30% of original wound. Meanwhile, CCL2 injection improved wound closure with unhealed area of 40% compared to PBS injection which were still at 100% of the initial surface. Neo-epidermal tongues of CCL2 injected wounds were significantly longer than PBS injected wounds. CCL2 also recruited more than double of fetal cells to wound bed compared to PBS, as demonstrated by FACS analysis. There was also a significant increase in epidermal and dermal cell proliferation, blood vessel angiogenesis and VEGF-A, VEGFR1 and VEGFR2 gene expression in wounds injected with CCL2 compared to PBS. Meanwhile, lymphogenesis as measured by LYVE1$^+$ lymphatic vessel density as well as VEGF-C, VEGFR3 gene expression, and inflammation, as measured by the number of GR1$^+$ and F4/80$^+$ cells in granulation tissue demonstrated no difference. Therefore, CCL2 recruit FMCs and improve delayed wound healing in postpartum mice.

EXAMPLE 2

Results

Figure 7A:
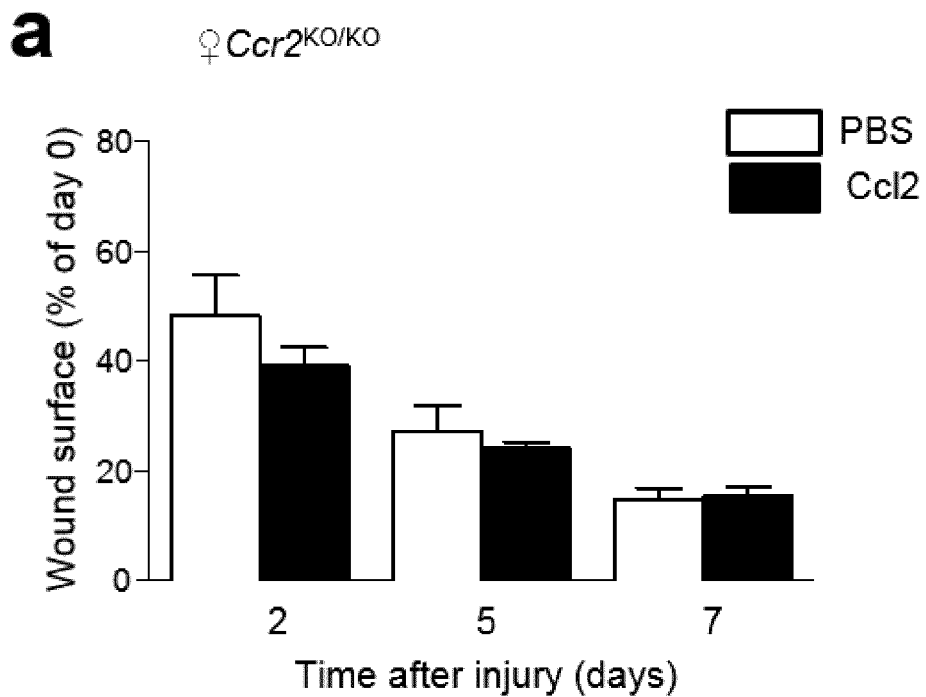
Figure 7B:
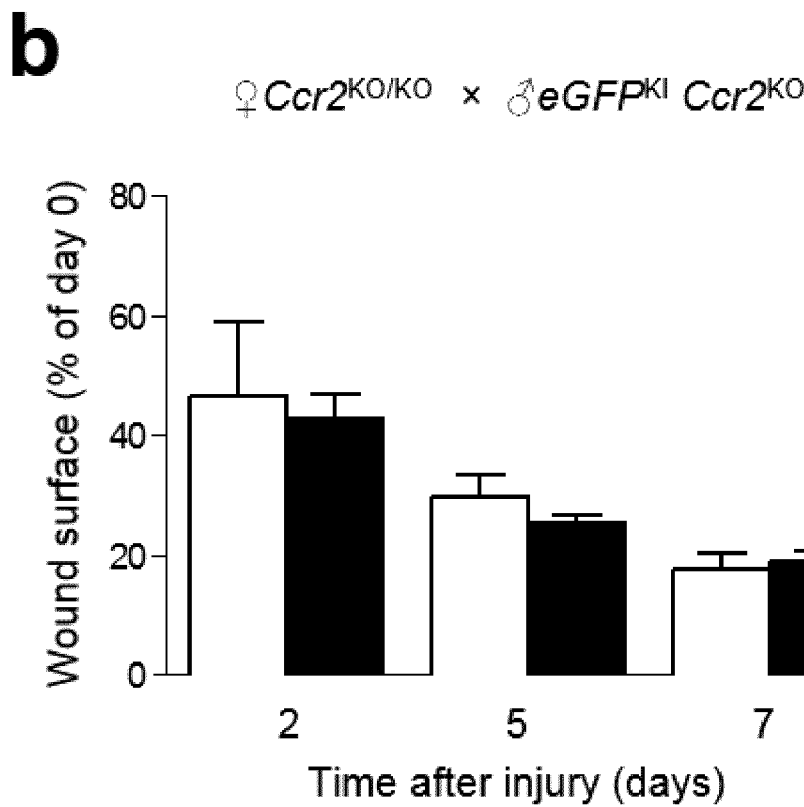
Figure 7C:
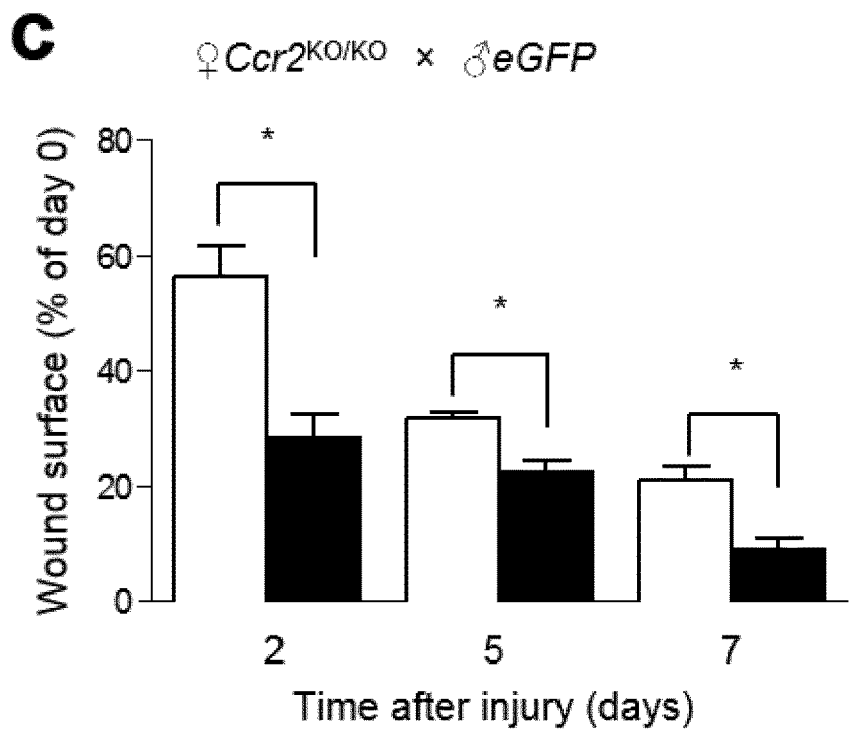
Figure 7D:
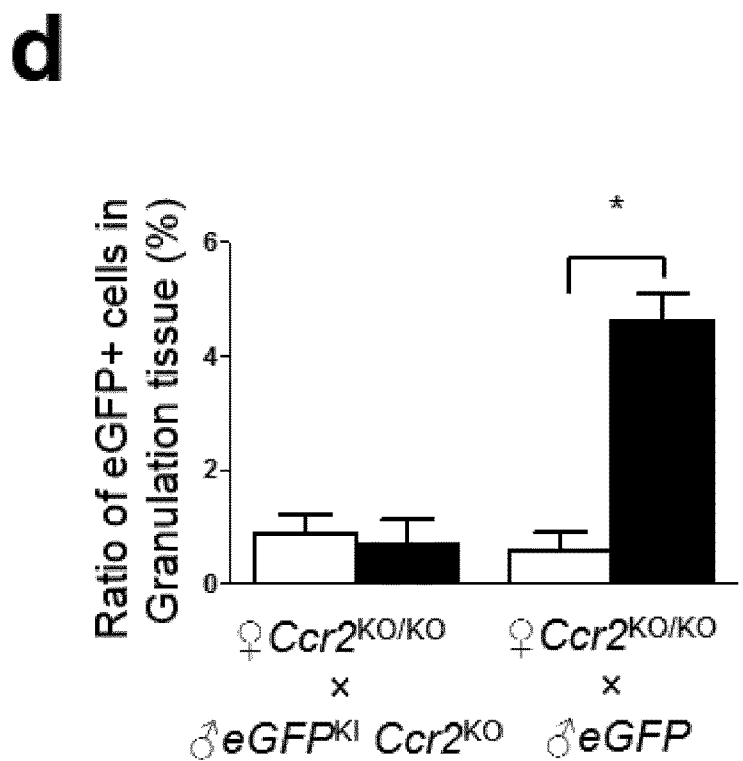

The Mobilization of FMCs to Maternal Tissues Through Ccl2 is Mediated by Ccr2 Receptor on Fetal Cells Once we showed that Ccl2 was able to recruit FMCs to injected maternal tissue, it was important to demonstrate whether the fetal cell signaling was dependent on Ccr2. To answer this question, we analyzed virgin female Ccr2$^{KO/KO}$ mice, female Ccr2$^{KO/KO}$ mice mated with eGFP$^+$ males and female Ccr2$^{KO/KO}$ mice mated with eGFP$^{KI}$ Ccr2$^{KO}$ males (FIG. 7 a,b). When Ccr2$^{KO/KO}$ female mice bear Ccr2$^{KO/KO}$ fetuses, the Ccl2 injections do not modify wound healing at any day (FIG. 7b). In contrast, when Ccr2$^{KO/KO}$ female mice bear Ccr2$^{WT/KO}$ fetuses, Ccl2 decreases wounded area by 49.08, 28.96 and 57.58% at days 2, 5 and 7 respectively (FIG. 7c). Interestingly, this ratio is similar to the ratio we found with Ccl2 in WT mice. In addition, only Ccr2$^{KO/KO}$ mice bearing Ccr2$^{WT/KO}$ fetuses displayed an increase in fetal cell infiltrate in granulation tissue upon Ccl2 local injections (FIG. 7d). Finally, the virgin Ccr2$^{KO/KO}$ mice did not show any change when treated with Ccl2 (FIG. 7a). Therefore, all these data demonstrate that Ccl2 enhances wound healing through Ccr2-dependent fetal cell recruitment to wound bed.

Figure 8A:
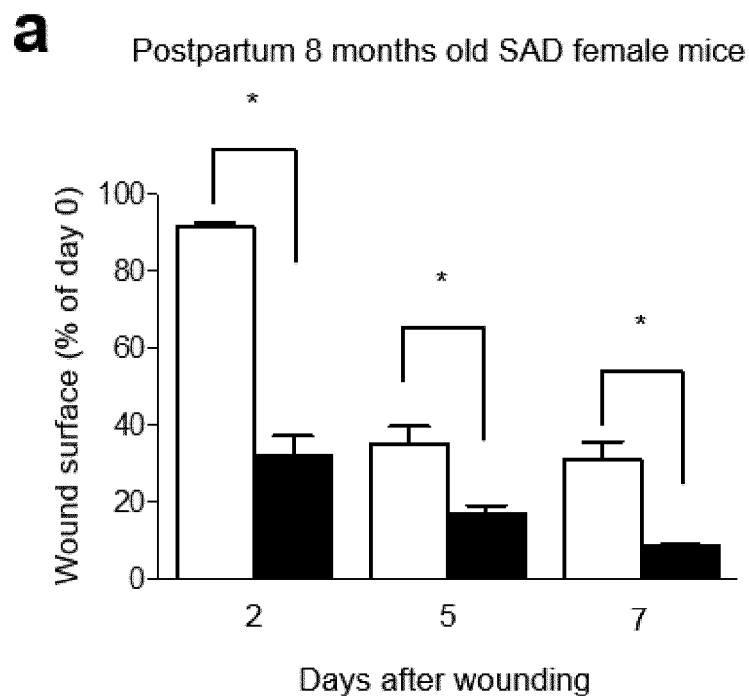
Figure 8B:

Low Doses ("Physiological") Doses of Ccl2 Improves Delayed Wound Healing in Post Parous Old "Sickle Cell" SAD Mice Sickle cell anemia may be complicated by prolonged ulcers. Nguyen V T el al., have recently developed a murine model of such chronic wounds, by performing wounds on old SAD mice (Nguyen V T et al., J Invest Dermatol, 2016, 136(2):497-506). We have therefore mated young female SAD mice with eGFP$^+$ WT males. Then the postpartum female SAD were allowed to age until 8 months, a time when these mice have a delayed wound healing. We have afterwards performed 8 mm wounds in such post-partum old SAD mice (n=3) or same age virgin old SAD females. At days 0 and 2, 50 ng of Ccl2 was injected in wounds of these mice as previously done. Analysis of wound closure showed that Ccl2 induced a significant improvement of healing kinetics in post-partum treated mice at days 2, 5 and 7 (FIG. 8a). Interestingly, and as observed previously for the two other models, in virgin SAD wounds; Ccl2 did not modify healing kinetics (FIG. 8b). These results indicate that in a murine model of sickle cell anemia, Ccl2 treatment of post-partum mice induces an intense mobilization of FMCs that results in a 73% reduction in wound area.

Ccl2 Improves FMCs Recruitment after Liver Injury

In order to determine whether "natural stem therapy" with recruitment of fetal cells may allow improvement of other maternal tissues than the skin, we studied liver fate after hepatectomy. Median lobe hepatectomy was performed in C57/Bl6 post-partum females previously mated with eGFP C57/Bl6 males. Ccl2 50 ng was injected in the hepatectomy site in 3 animals while PBS was injected in 3 others. Mice were sacrificed 7 days later. Livers were harvested. Cryosections allowed the analysis of eGFP fetal cells. The percentage of such cells was 3.1% under PBS injection, while it reached 8.5% in Ccl2 treated livers (p<0.018) (FIG. 9a). This result shows that in liver repair, Ccl2 leads also to the recruitment of fetal cells.

Figure 10A:
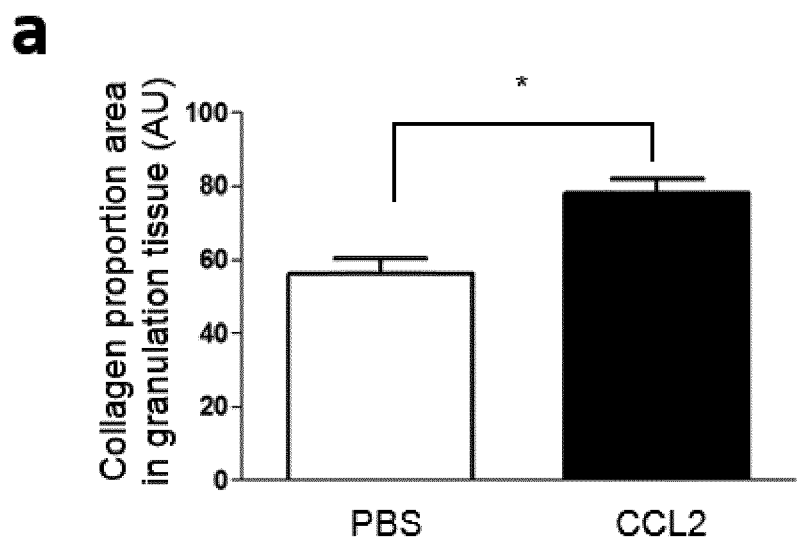
Figure 10B:
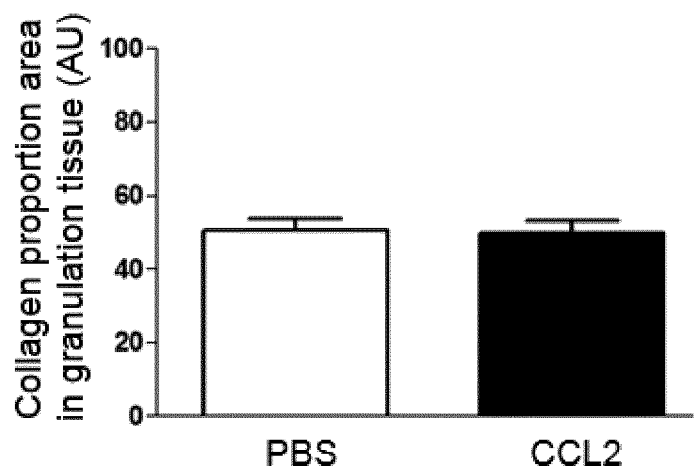
Figure 10C:
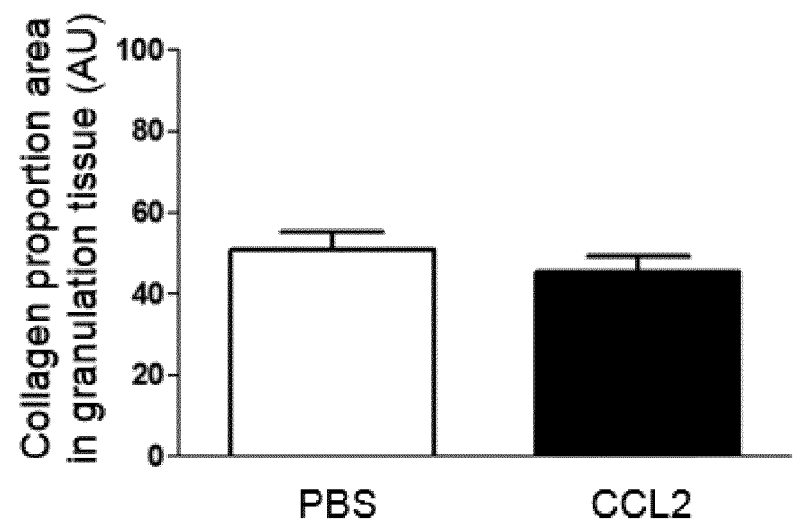
Figure 10D:
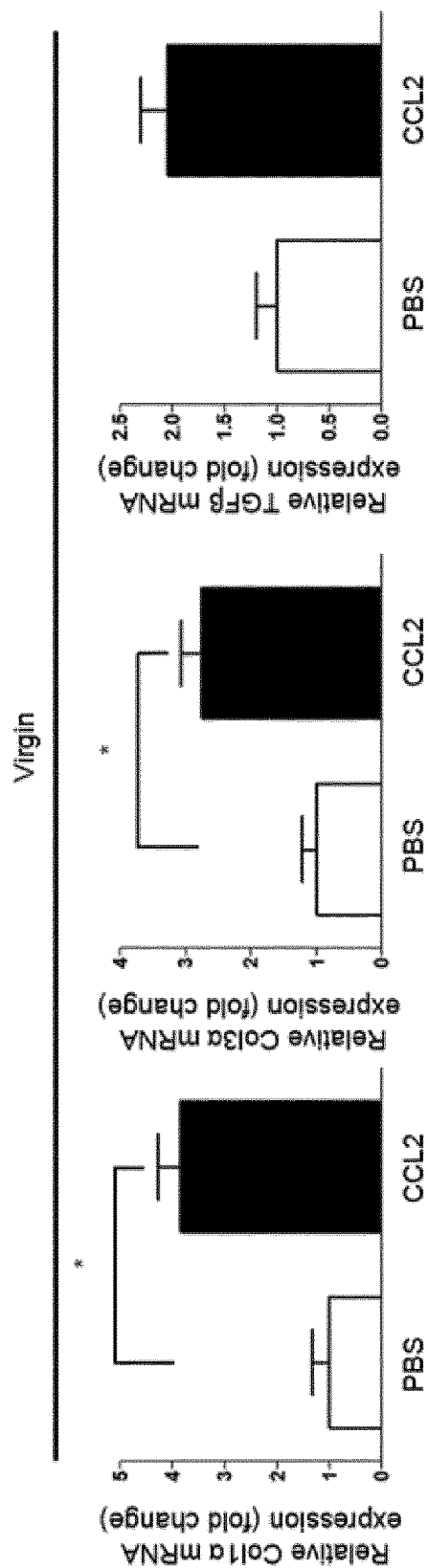
Figure 10E:
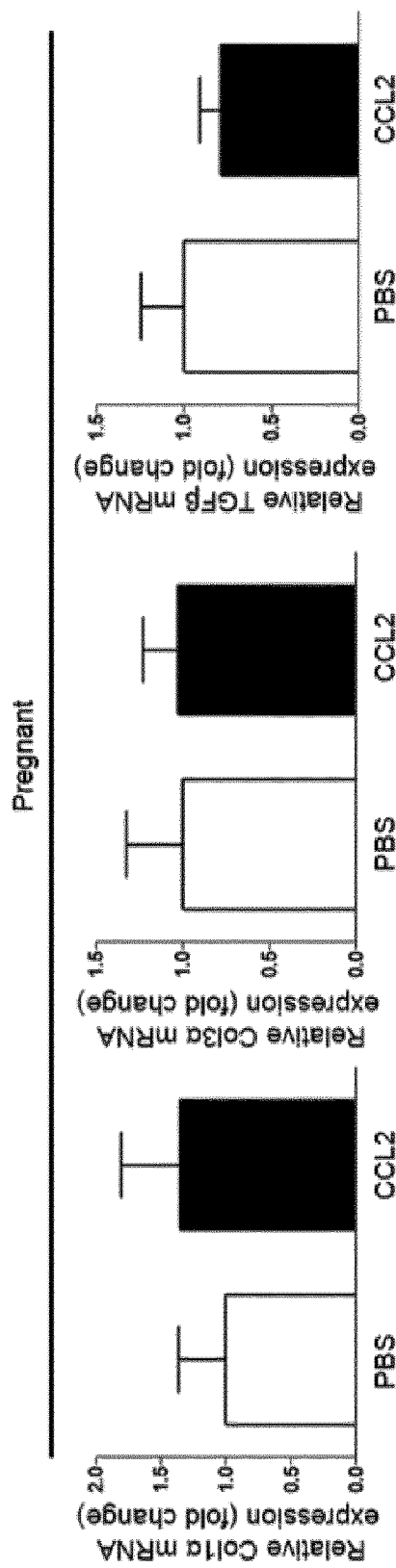
Figure 10F:
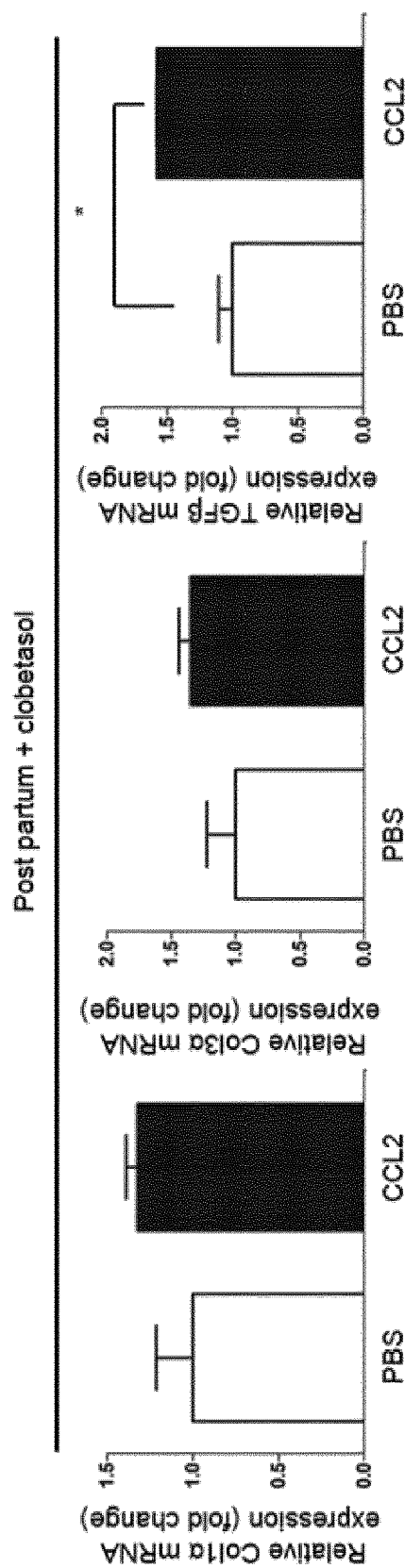

Low Doses of Ccl2 in Pregnant and Post-Partum Mice Improves Wound Healing without Fibrosis Finally, an important question remains the difference in the mechanisms observed with the low doses of Ccl2 used. Indeed, when Ccl2 is given at higher dosages in virgin animals in other settings than wound healing, recruitment of monocytes with risks of fibrosis was noted. We have therefore studied skin and liver post Ccl2 injections in wounds. In pregnant and post-partum clobetasol pretreated mice, Ccl2 wound injections lead to a reduced dermal fibrosis at day 7 post wounding as assessed through Sirius red staining (FIG. 10a-c). Collagen and 3 mRNAs levels analyzed through RT-PCR, in dermal day 7 wounds showed that Ccl2 led to a reduction of these messengers. In contrast, Ccl2 in wounds of virgin mice induced an increase of dermal fibrosis (FIG. 10d-f) as well as an increase in Collagen 1 and 3 mRNA levels. These results clearly show that low physiological doses of Ccl2 injected in wounds do not induce adult mono-macrophage recruitment with fibrosis, but rather FMPCs infiltration.

In summary, our results indicate that in the absence of any deficiency in the CCR2/CCL2 axis, CCL2 given early, at low doses in wounds are able to improve angiogenesis through the mobilization of certain fetal cell population CD34+CD11b+CD31+ (FMPCs). In our hands, these cells (or fetal cells) express CCR2 on their surface with levels 100 times higher than their adult equivalents.

Our result agrees with (a) the absence of increase of F480 macrophages at various time points in CCL2 treated post-partum mice, and the absence of the profibrotic effect reported with high CCL2 (b) previous studies showing no improvement of a normal skin wound repair when high doses of CCL2 are injected in virgin mice (Dipietro et al., Wound Repair and Regeneration, 2001).

REFERENCES

Throughout this application, various references describe the state of the art to which this invention pertains. The disclosures of these references are hereby incorporated by reference into the present disclosure.

The invention claimed is:

1. A method of treating a tissue lesion in a subject in need thereof comprising administering to the subject a therapeutically effective amount of a CCR2 agonist,
   wherein the subject is a female who is pregnant or has been pregnant at least one time,
   wherein the CCR2 agonist comprises a polypeptide having the identity of SEQ ID NO:3, and
   wherein the therapeutically effective amount of the CCR2 agonist is sufficient to mediate recruitment of fetal myeloid progenitor cells (FMPCs) from blood circulation to the tissue lesion.

2. The method of claim 1 wherein the CCR2 agonist comprising the polypeptide is an immunoadhesin.

3. The method according to claim 1, wherein the tissue lesion is selected from the group consisting of skin lesion, hepatic lesion, cardiac lesion, lung lesion, neurologic lesion, ocular lesion, stomach lesion, pancreas lesion, spleen lesion, bowel lesion, thyroid lesion, thymus lesion, kidney lesion, artery lesion, vein lesion, bone lesion, bone marrow lesion, muscle lesion, tendon lesion, ligament lesion, reproductive organs lesion and endocrine glands lesion.

4. The method according to claim 1, wherein the tissue lesion is a diabetic foot ulcer resulting from diabetes.

5. The method according to claim 1, wherein the tissue lesion is a leg ulcer resulting from sickle-cell anemia.

6. The method according to claim 1, wherein a conventional treatment of tissue lesions is also administered to the subject.

7. A method of treating a tissue lesion in a female subject in need thereof, wherein the female subject is pregnant or has been pregnant at least one time, comprising the step of administering to the female subject a therapeutically effective amount of a CCR2 agonist comprising a polypeptide having the amino acid sequence identity of SEQ ID NO:3,
wherein the therapeutically effective amount of the CCR2 agonist is sufficient to
recruit fetal myeloid progenitor cells (FMPCs) from blood circulation to the tissue lesion, and
promote neovascularization in the tissue lesion.

8. The method according to claim 7, wherein the tissue lesion is selected from the group consisting of skin lesion, hepatic lesion, cardiac lesion, lung lesion, neurologic lesion, ocular lesion, stomach lesion, pancreas lesion, spleen lesion, bowel lesion, thyroid lesion, thymus lesion, kidney lesion, artery lesion, vein lesion, bone lesion, bone marrow lesion, muscle lesion, tendon lesion, ligament lesion, reproductive organs lesion and endocrine glands lesion.

9. The method according to claim 7, wherein the tissue lesion is a diabetic foot ulcer resulting from diabetes.

10. The method according to claim 7, wherein the tissue lesion is a leg ulcer resulting from sickle-cell anemia.

11. The method according to claim 7, wherein a conventional treatment of tissue lesions is also administered to the subject.

* * * * *

SEQUENCE LISTING

```
<160> NUMBER OF SEQ ID NOS: 3

<210> SEQ ID NO 1
<211> LENGTH: 374
<212> TYPE: PRT
<213> ORGANISM: Homo sapiens

<400> SEQUENCE: 1

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45

Tyr Ser Leu Val Phe Ile Phe Gly Phe Val Gly Asn Met Leu Val Val
    50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205
```

Leu Gly Leu Val Leu Pro Leu Ile Met Val Ile Cys Tyr Ser Gly
            210                 215                 220

Ile Leu Lys Thr Leu Arg Cys Arg Asn Glu Lys Arg His Arg
225                 230                 235                 240

Ala Val Arg Val Ile Phe Thr Ile Met Ile Val Tyr Phe Leu Phe Trp
                    245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Gln Leu Asp Gln Ala Thr Gln
            275                 280                 285

Val Thr Glu Thr Leu Gly Met Thr His Cys Cys Ile Asn Pro Ile Ile
290                 295                 300

Tyr Ala Phe Val Gly Glu Lys Phe Arg Ser Leu Phe His Ile Ala Leu
305                 310                 315                 320

Gly Cys Arg Ile Ala Pro Leu Gln Lys Pro Val Cys Gly Gly Pro Gly
                    325                 330                 335

Val Arg Pro Gly Lys Asn Val Lys Val Thr Thr Gln Gly Leu Leu Asp
                    340                 345                 350

Gly Arg Gly Lys Gly Lys Ser Ile Gly Arg Ala Pro Glu Ala Ser Leu
            355                 360                 365

Gln Asp Lys Glu Gly Ala
            370

<210> SEQ ID NO 2
<211> LENGTH: 360
<212> TYPE: PRT
<213> ORGANISM: Homo sapiens

<400> SEQUENCE: 2

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
                20                  25                  30

His Lys Phe Asp Val Lys Gln Ile Gly Ala Gln Leu Leu Pro Pro Leu
            35                  40                  45

Tyr Ser Leu Val Phe Ile Phe Gly Phe Val Gly Asn Met Leu Val Val
50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile

```
                    195                 200                 205
Leu Gly Leu Val Leu Pro Leu Leu Ile Met Val Ile Cys Tyr Ser Gly
        210                 215                 220
Ile Leu Lys Thr Leu Leu Arg Cys Arg Asn Glu Lys Lys Arg His Arg
225                 230                 235                 240
Ala Val Arg Val Ile Phe Thr Ile Met Ile Val Tyr Phe Leu Phe Trp
                245                 250                 255
Thr Pro Tyr Asn Ile Val Ile Leu Leu Asn Thr Phe Gln Glu Phe Phe
                260                 265                 270
Gly Leu Ser Asn Cys Glu Ser Thr Ser Gln Leu Asp Gln Ala Thr Gln
                275                 280                 285
Val Thr Glu Thr Leu Gly Met Thr His Cys Cys Ile Asn Pro Ile Ile
                290                 295                 300
Tyr Ala Phe Val Gly Glu Lys Phe Arg Arg Tyr Leu Ser Val Phe Phe
305                 310                 315                 320
Arg Lys His Ile Thr Lys Arg Phe Cys Lys Gln Cys Pro Val Phe Tyr
                325                 330                 335
Arg Glu Thr Val Asp Gly Val Thr Ser Thr Asn Thr Pro Ser Thr Gly
                340                 345                 350
Glu Gln Glu Val Ser Ala Gly Leu
                355                 360

<210> SEQ ID NO 3
<211> LENGTH: 99
<212> TYPE: PRT
<213> ORGANISM: Homo sapiens

<400> SEQUENCE: 3

Met Lys Val Ser Ala Ala Leu Leu Cys Leu Leu Leu Ile Ala Ala Thr
1               5                   10                  15
Phe Ile Pro Gln Gly Leu Ala Gln Pro Asp Ala Ile Asn Ala Pro Val
                20                  25                  30
Thr Cys Cys Tyr Asn Phe Thr Asn Arg Lys Ile Ser Val Gln Arg Leu
                35                  40                  45
Ala Ser Tyr Arg Arg Ile Thr Ser Ser Lys Cys Pro Lys Glu Ala Val
        50                  55                  60
Ile Phe Lys Thr Ile Val Ala Lys Glu Ile Cys Ala Asp Pro Lys Gln
65                  70                  75                  80
Lys Trp Val Gln Asp Ser Met Asp His Leu Asp Lys Gln Thr Gln Thr
                85                  90                  95
Pro Lys Thr
```